US009636458B2

(12) United States Patent
Hoffman et al.

(10) Patent No.: US 9,636,458 B2
(45) Date of Patent: May 2, 2017

(54) MULTI-BARREL SYRINGE INJECTION SYSTEM

(71) Applicant: Muffin Incorporated, West Lafayette, IN (US)

(72) Inventors: Grant T. Hoffman, Akron, OH (US); Robert Eells, Bloomington, IN (US); Wen Hong Neoh, Bloomington, IN (US); Jeffry S. Melsheimer, Bloomington, IN (US)

(73) Assignee: Muffin Incorporated, West Lafayette, IN (US)

( * ) Notice: Subject to any disclaimer, the term of this patent is extended or adjusted under 35 U.S.C. 154(b) by 279 days.

(21) Appl. No.: 14/603,613

(22) Filed: Jan. 23, 2015

(65) Prior Publication Data

US 2015/0141956 A1 May 21, 2015

Related U.S. Application Data

(63) Continuation of application No. PCT/US2013/051805, filed on Jul. 24, 2013.

(Continued)

(51) Int. Cl.
  *A61M 5/19* (2006.01)
  *A61M 5/31* (2006.01)
  *A61M 5/32* (2006.01)

(52) U.S. Cl.
  CPC ............ *A61M 5/19* (2013.01); *A61M 5/3137* (2013.01); *A61M 5/3295* (2013.01); *A61M 5/3297* (2013.01); *A61M 2205/19* (2013.01)

(58) Field of Classification Search
  CPC .... A61M 5/19; A61M 5/3137; A61M 5/3295; A61M 5/3297; A61M 2205/19

(Continued)

(56) References Cited

U.S. PATENT DOCUMENTS 2,865,371 A * 12/1958 Dorbecker ........ A61M 5/14526
  222/25
3,872,864 A * 3/1975 Allen, Jr. .......... A61M 5/31596
  604/89

(Continued)

FOREIGN PATENT DOCUMENTS

WO  WO 92/10142  6/1992
WO  98/13094 A1  4/1998

(Continued)

OTHER PUBLICATIONS

International Search Report and Written Opinion issued in PCT/US2013/051805, dated Oct. 24, 2013.

*Primary Examiner* — Manuel Mendez
(74) *Attorney, Agent, or Firm* — Woodard Emhardt Moriarty McNett & Henry LLP

(57) ABSTRACT

An injection device for injecting a medicant into a plurality of tissue sites in a patient for a selected treatment is constructed and arranged such that the number of tissue sites is the total number for the selected treatment thereby requiring a single positioning step. The injection device includes a body having a syringe and a control linkage, the syringe including a plurality of barrels, and a cooperating plunger array including a plurality of plungers. Each barrel receives a corresponding plunger. The injection device further includes a plurality of injection needles connected to the syringe wherein one injection needle is connected to each barrel, a multi-lumen tip, a shaft connected to the multi-lumen tip and extending between said multi-lumen tip and said body. The control linkage is connected to each needle so as to move each needle between a deployed injection position and a retracted position.

30 Claims, 30 Drawing Sheets

Related U.S. Application Data

(60) Provisional application No. 61/675,936, filed on Jul. 26, 2012.

(58) Field of Classification Search
USPC .............. 604/191, 164.01, 164.04, 173, 506
See application file for complete search history.

(56) References Cited

U.S. PATENT DOCUMENTS

| | | | |
|---|---|---|---|
| 4,136,695 A * | 1/1979 | Dafoe | A61F 6/225 128/831 |
| 4,359,049 A * | 11/1982 | Redl | A61B 17/00491 604/191 |
| 5,354,279 A * | 10/1994 | Hofling | A61M 25/0069 604/164.12 |
| 5,419,777 A | 5/1995 | Hofling | |
| 5,549,644 A * | 8/1996 | Lundquist | A61M 25/0136 604/22 |
| 5,720,719 A | 2/1998 | Edwards et al. | |
| 5,997,507 A * | 12/1999 | Dysarz | A61M 25/0631 604/110 |
| 6,302,870 B1 * | 10/2001 | Jacobsen | A61B 17/22 604/164.09 |
| 7,621,895 B2 | 11/2009 | Willis et al. | |
| 8,012,139 B2 | 9/2011 | McKay et al. | |
| 8,083,722 B2 | 12/2011 | McKay | |
| 2006/0041243 A1 | 2/2006 | Nayak et al. | |
| 2006/0259006 A1 | 11/2006 | McKay et al. | |
| 2007/0088268 A1 | 4/2007 | Edwards | |
| 2007/0203474 A1 | 8/2007 | Ryan et al. | |
| 2011/0137250 A1 | 6/2011 | Kraft | |
| 2012/0071832 A1 | 3/2012 | Bunch | |

FOREIGN PATENT DOCUMENTS

| | | |
|---|---|---|
| WO | WO 2009/023798 A2 | 2/2009 |
| WO | WO 2012/135537 A2 | 10/2012 |

* cited by examiner

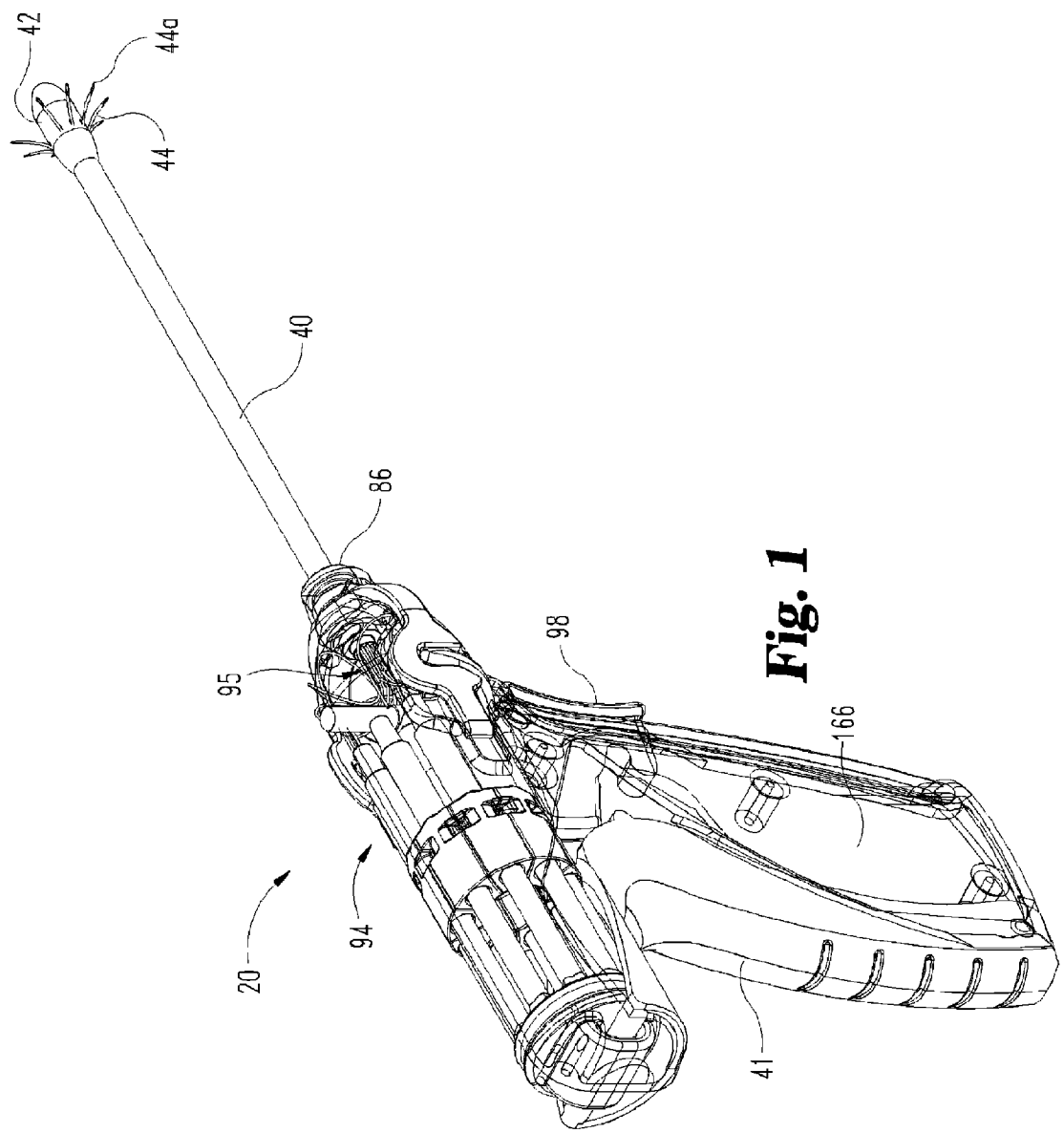

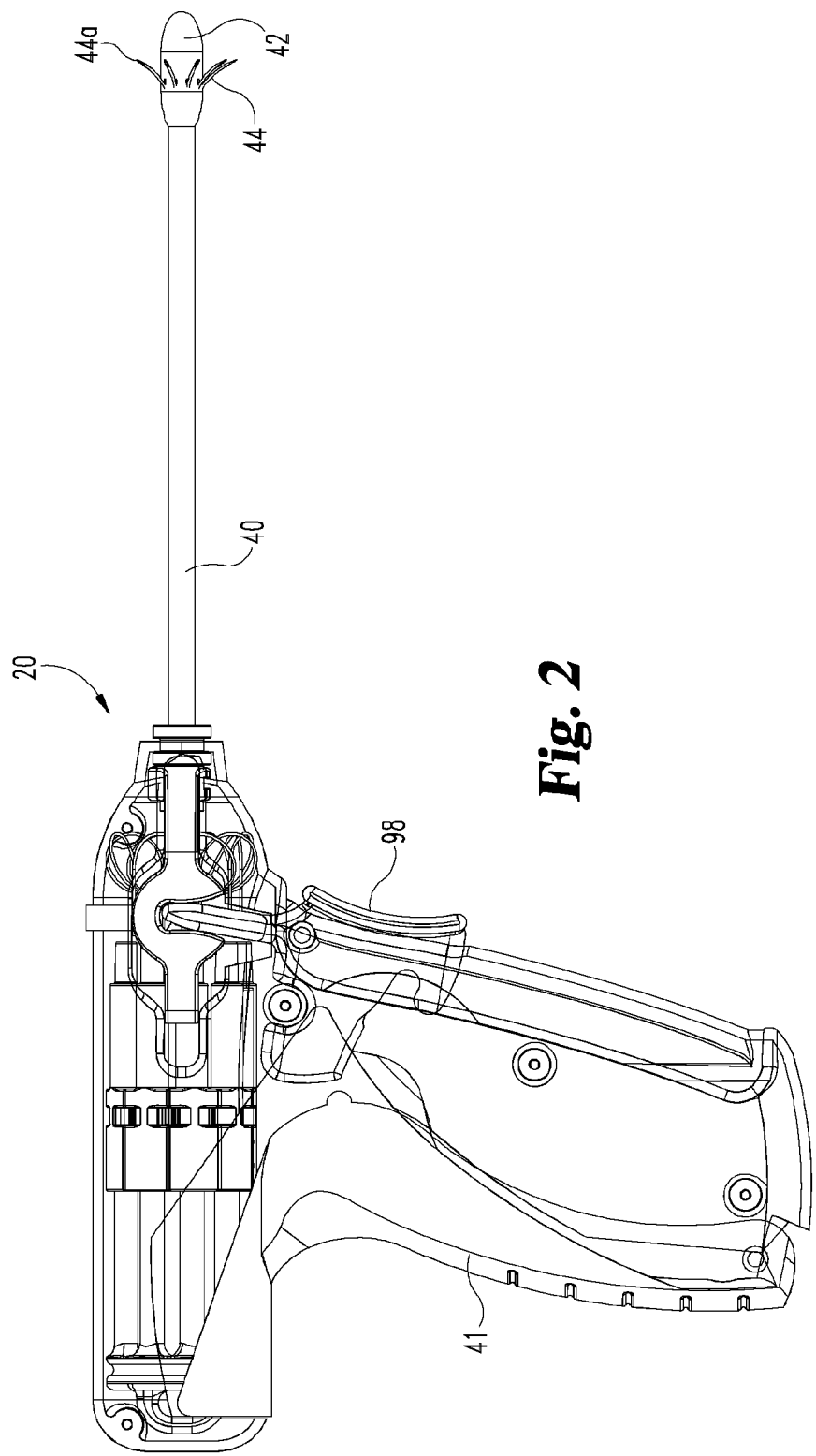

MULTI-BARREL SYRINGE INJECTION SYSTEM

CROSS-REFERENCE TO RELATED APPLICATIONS

This application is a continuation of International Application No. PCT/US2013/051805 filed Jul. 24, 2013, which claims the benefit of U.S. Provisional Application No. 61/675,936 filed Jul. 26, 2012, which are incorporated herewith by reference.

BACKGROUND

Injection needle devices and systems are used to inject a medicant into a tissue site of a patient. One current style of injection needle device uses a plurality of needles, for example three (3). When the desired number of injection sites into the tissue is greater than the number of needles provided as part of the injection needle device, multiple injection cycles must be performed. In order to perform a second injection cycle with the device, it is necessary to turn, rotate or reposition the device so that the needles of the device are aligned with additional tissue sites which are intended to receive an injection of the medicant. This repositioning requires that the extended or deployed needles first be retracted or withdrawn so as not to extend from the tip of the device and then, depending on the tissue site, the tip of the device may have to be partially retracted in order to be turned and repositioned before the needles are once again deployed (i.e. extended from the tip) for injection of the medicant into other tissue sites.

The tip of the injection device which is intended to be positioned adjacent the tissue site, includes an array of apertures which receive the injection needles. A mechanical deployment structure is used to extend the pointed and open tips of the needles (one (1) needle per aperture) for the injection of medicant and in order to retract the tips of the needles when the device is not in use and/or when the device is being repositioned for a second or subsequent injection cycle.

In one example of an earlier injection device, there are three (3) injection needles and the selected injection procedure includes nine (9) desired tissue injection sites. A specific use of this earlier device would be for the injection of autologous derived cells into the urinary sphincter of a patient for the treatment of stress urinary incontinence (SUI). In order to deliver medicant to each of the nine (9) tissue injection sites, three (3) injection cycles must be performed. A degree of precision in the positioning and orientation of the device is required and the desired degree of precision is difficult to exercise. The tip of the device is held at the meatus of the sphincter while extending (i.e. deploying) the three (3) injection needles into the tissue. A delivery syringe in cooperation with a common manifold is used for delivering medicant from that common manifold to each of the three (3) injection needles. Assuming that the common manifold initially contains all of the medicant for the nine (9) tissue sites, it becomes important that manipulation of the delivery syringe be used in such a way that its plunger is only depressed approximately one-third (⅓) of its total travel in order to deliver the desired or correct dosage (approximately one-third) of cell-based treatment (i.e. the medicant) as part of the first injection cycle. This constitutes the first cycle of three (3) and is completed when the three (3) needles are withdrawn into the tip of the device so that the device can be repositioned for the second injection cycle to be performed. Part of the repositioning of the device for the second cycle requires that the device be rotated so as to reposition the three (3) needles, actually the three (3) needle apertures since the needle tips have been retracted, to the desired location of three (3) new tissue sites for the next three (3) injections into those sites. At this second position for the second injection cycle, the three (3) needles of the device are extended or deployed into the tissue and the common syringe plunger is depressed another one-third (⅓) of its travel into the common manifold. This is intended to deliver the second one-third (⅓) of the medicant at these three (3) new tissue sites. Six (6) of the nine (9) selected injection sites have now received an injection of the medicant, presumably the scheduled dosage of the medicant. The third and final cycle is essentially a repeat of the second cycle. This third cycle begins when the device is rotated to the position where the three (3) needle apertures are aligned with the final three (3) injection sites. The needles are then deployed for medicant injections into the final three (3) tissue sites.

One of the concerns with the type of injection device which has been described is that it uses a separate syringe which is suspended from a luer connection at its proximal end. This assembly approach presents a concern regarding the structural integrity of the connection. A further concern with this type of earlier injection device, as described, is the use of a manifold to flow couple the three (3) needles to be syringe. The use of a manifold in this context may introduce turbulence and an inconsistent distribution of the medicant. Another concern is the use of a separate syringe and the inability to purge air from the system. Further, with the need for and use of long needle cannulas, the volume of the cannulas becomes a concern.

The type of injection device which has been described as being representative of some earlier constructions, includes a manifold or reservoir for the medicant and the manifold is either directly or indirectly connected to each of the three (3) needles which are arranged in parallel. A single plunger is cooperatively arranged with the manifold for pushing the medicant into and through each needle. If one tissue site is more dense than another tissue site, the amount of medicant which is injected at each site will not be equal. If individual syringe barrels are associated with each needle and if each barrel has its own cooperating plunger and piston, then this inequality problem in medicant distribution among the selected tissue sites would be solved. This is the selected structure which is disclosed herein in the exemplary embodiment.

The various design issues and concerns which are outlined above are the focus of the embodiments of the present disclosure. The preferred embodiment incorporates a multi-barrel syringe and a needle count which corresponds to the number of desired tissue injection sites for the particular treatment. Cooperating elements and structures of the multi-barrel syringe provide other design features which are considered to be novel and unobvious relative to the current state of the art.

SUMMARY

In at least one embodiment of the present disclosure, a multi-barrel syringe is provided, as part of an injection system, for injecting a medicant into a plurality of tissue injection sites in a patient.

An injection device for injecting a medicant into a plurality of tissue sites in a patient for a selected treatment is disclosed wherein the number of tissue sites is the total number for the selected treatment thereby requiring a single positioning step. The injection device includes a body having a syringe and a control linkage, the syringe including a plurality of barrels, and a cooperating plunger array including a plurality of plungers, wherein each barrel receives a corresponding plunger. The injection device further includes a plurality of injection needles connected to the syringe wherein one injection needle is connected to each barrel, a multi-lumen tip, a shaft connected to the multi-lumen tip and extending between the multi-lumen tip and the body, the shaft receiving a portion of each injection needle. Wherein the control linkage is connected to each needle and is constructed and arranged to move each needle relative to the multi-lumen tip between a deployed injection position and a retracted position, wherein the number of needles is at least as great as the number of tissue sites for the selected treatment.

An injection system for injecting a medicant into a plurality of tissue sites in a patient for a selected treatment is disclosed wherein the number of tissue sites is the total number for the selected treatment thereby requiring a single positioning step. The injection system includes a filling syringe, a charge of medicant loaded into the filling syringe, and an injection device. The injection device includes a body having a plurality of barrels, a plurality of injection needles, wherein each needle is connected to a corresponding barrel, a multi-lumen tip for positioning an open tip of each injection needle at a corresponding one of the injection sites, means for connecting the multi-lumen tip with the body and means for moving each injection needle of between a deployed, injection position and a retracted position.

A method of preparing for use and using an injection device for injecting a medicant into a plurality of tissue sites in a patient for a selected treatment is disclosed. The method includes the steps of providing a filling syringe, providing a charge of medicant for delivery by the filling syringe, providing an injection device having a plurality of barrels, a plunger array, a plurality of injection needles with one needle connected to each barrel, an injection tip which receives an open tip of each injection needle and means for moving each injection needle to a deployed injection position, inserting the filling syringe into the injection device, filling each syringe with medicant, moving the plunger array to purge air from within the plurality of injection needles, retracting the open tip portion of each needle, positioning the injection tip at the tissue sites, moving each injection needle to a deployed injection position into its corresponding tissue site and moving the plunger array to inject medicant into each tissue site.

BRIEF DESCRIPTION OF THE DRAWINGS

FIG. 1 is a perspective view of a multi-barrel syringe injection device according to the present disclosure, with one half of a transparent housing.

FIG. 2 is a right side elevational view of the FIG. 1 injection device.

DESCRIPTION OF THE SELECTED EMBODIMENTS

Figure 1A:
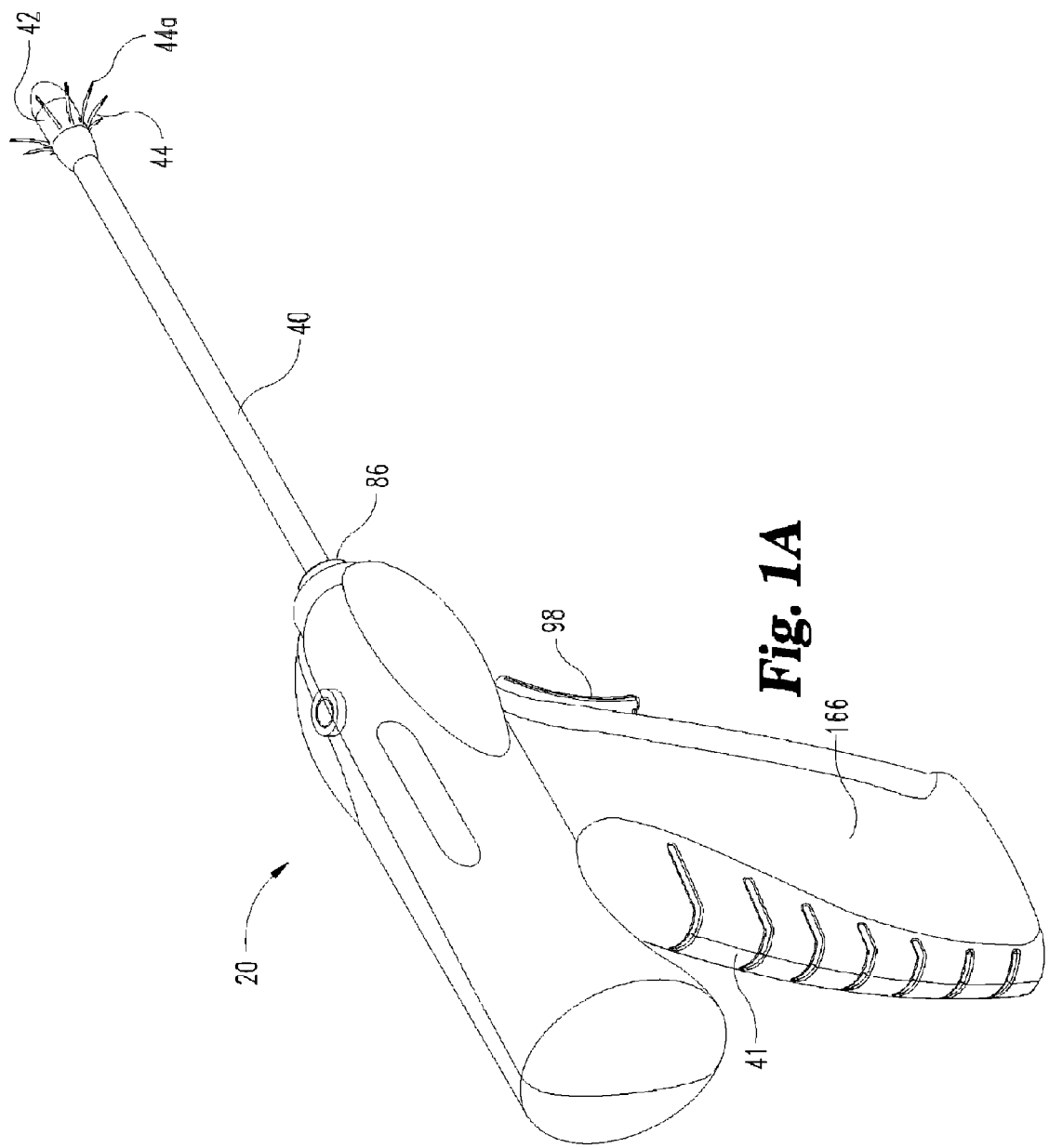
FIG. 1A is a perspective view of a multi-barrel syringe injection device corresponding to the FIG. 1 injection device, with both halves of an opaque housing.
Figure 2A:
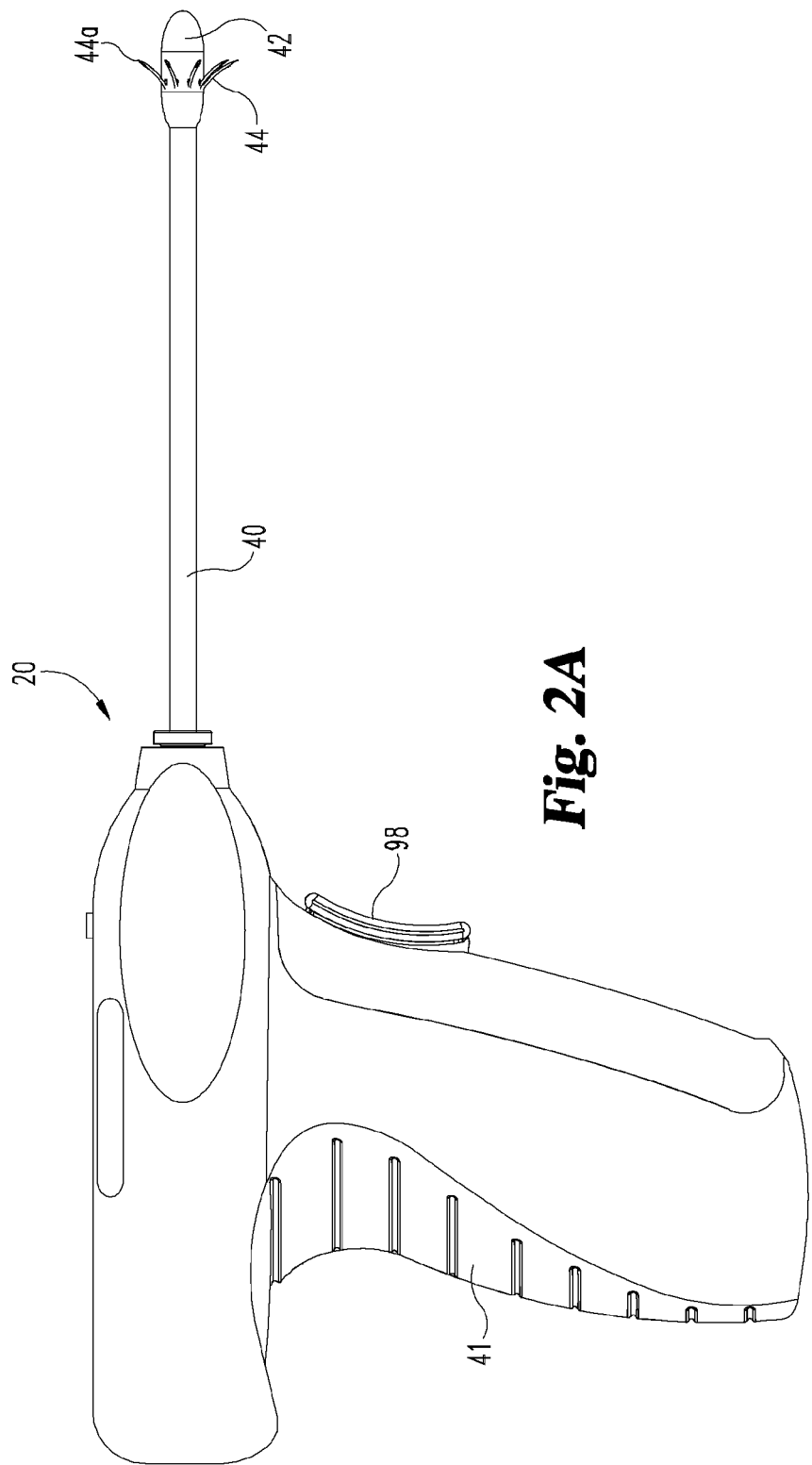
FIG. 2A is a right side elevational view of the FIG. 1A injection device.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

Figure 14:
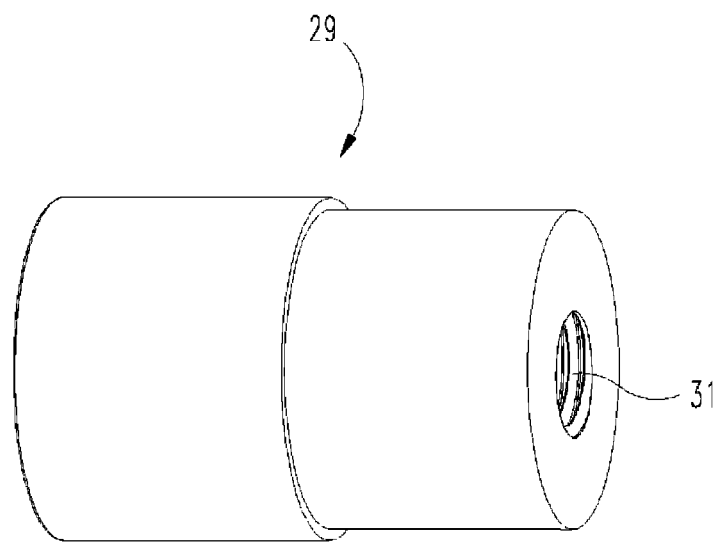
FIG. 14 is a distal perspective view of a hub which is one component part of the FIG. 1 injection device.
Figure 14A:
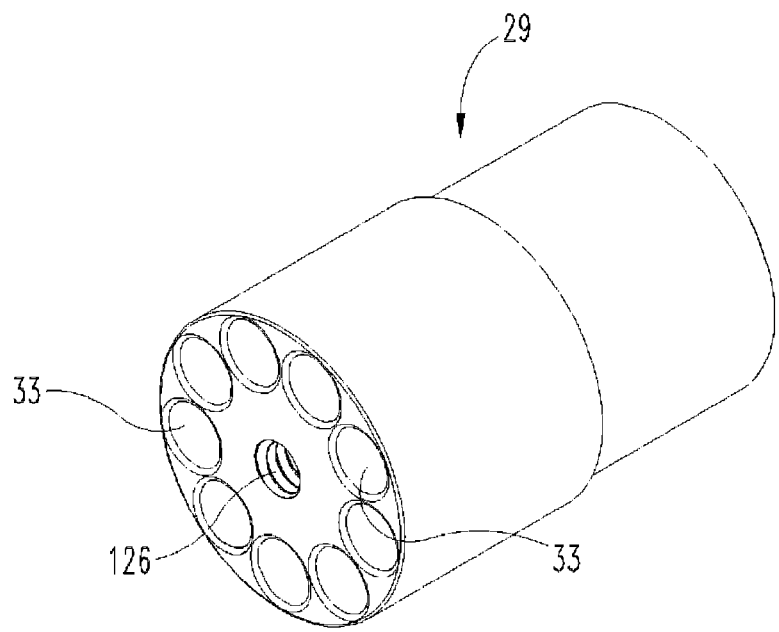
FIG. 14A is a proximal perspective view of the FIG. 14 hub.
Figure 14B:
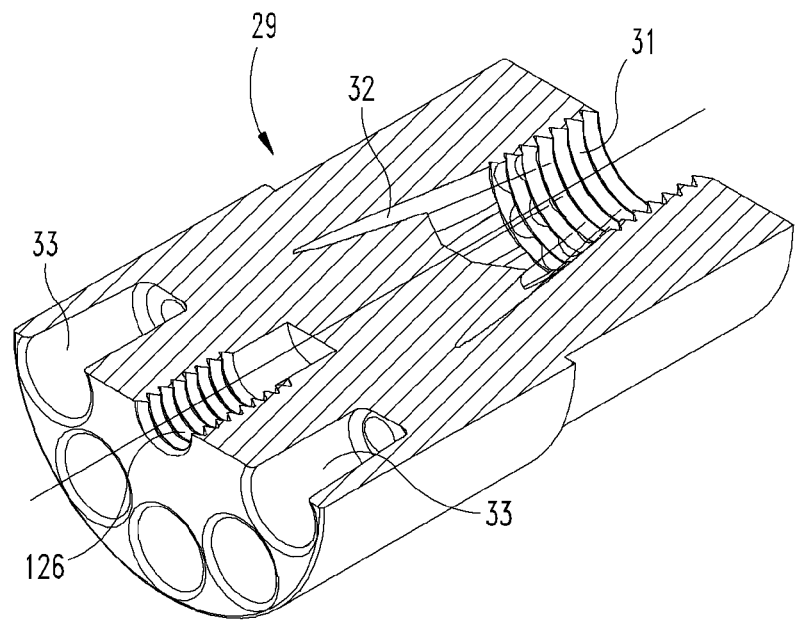
FIG. 14B is a proximal perspective view, in full section, of the FIG. 14 hub.
Figure 14C:
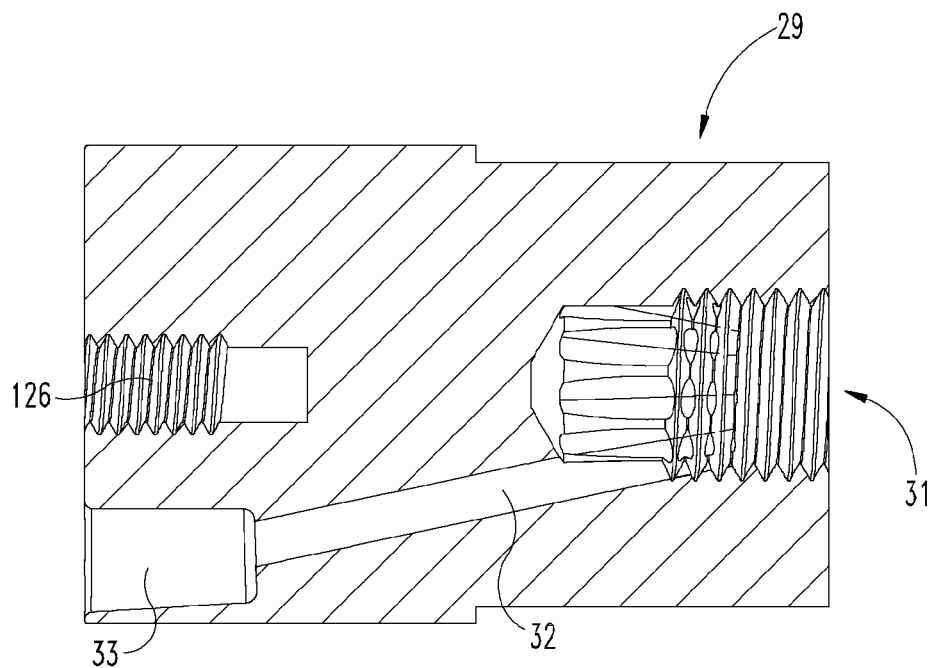
FIG. 14C is a side elevational view, in full section, of the FIG. 14 hub.

Referring to FIGS. 1-6A there is illustrated a multi-barrel syringe injection device 20 which constitutes the primary structural member of a multi-barrel syringe injection system. The use of "system" is intended to include, in addition to device 20, the medicant and the medicant-delivery syringe or similar device which connects to device 20 for introducing the initial charge of medicant into device 20 and for refilling or recharging of device 20 with additional medicant, if or as required. The manner of connection and the arrangement for the delivery of medicant is diagrammatically illustrated in FIG. 7. As is shown, delivery syringe 22 contains a volume of medicant 24. The tip 26 of syringe 22 is inserted into L-shaped adapter 28 with a luer connection. Depressing plunger 30 (in the direction of the arrow) delivers an initial charge of medicant 24 into device 20. With reference to FIGS. 8 and 8A, adapter 28 defines a continuous flow passageway 28a therethrough for the injected medicant from syringe 20 to flow through adapter 28 and then through manifold hub 29 (see FIGS. 14, 14A, 14B and 14C) into the medicant chamber 36 of each barrel 35, as will described in additional detail later in this disclosure. The externally-threaded, hollow post 27 of adapter 28 securely threads into the internally-threaded hole 31 of manifold hub 29. The specific storage and handling of this initial charge of medicant 24 by device 20 begins by injecting the medicant through adapter 28 and into the inlet end 31 of manifold hub 29. There are nine (9) passages 32 (see FIG. 14C) which connect the inlet end 31 to a corresponding barrel aperture 33. In the exemplary embodiment these nine (9) passages 32 are equally spaced for a more efficient utilization of the available space. The manifold configuration divides the single incoming flow of medicant into nine (9) branches. Each barrel aperture 33 establishes a luer connection with the filling tip 34 (and filling passage 34a) of each barrel 35, see FIGS. 16, 16A and 16B. The tapered fitting between aperture 33 and filling tip 34 is smaller than the "standard" luer, but uses essentially the same taper angle as the standard luer. Additional details of hub 29 and barrel 35 will be described later in this disclosure.

Upper end 28b of L-shaped adapter 28 extends beyond the body of device 20 as shown by the small protruding portion. Adapter 28 remains threadedly connected to manifold hub 29 after a charge of medicant 24 has been delivered to each medicant chamber 36. In order to keep debris out of upper end 28b and accordingly out of passageway 28a, a small cap (or plug), not illustrated, with a cooperative luer connection is connected into upper end 28b when the delivery syringe 22 is disconnected and removed after delivery of the medicant 24.

A "luer connection", as that phrase is used herein, refers to the use of a luer taper as part of a standardized system of small-scale fluid fittings used for making a leak-free connection between a male taper fitting and its mating femal part. There are two varieties which are generally referred to as "Luer-Lok®" and "Luer-Slip®". The first includes threads while the other relies on friction.

This disclosure includes several references to the connection, joining or attachment of one component part to another, or to others. When the connection, joining or attachment is intended to be secure (and/or establish a tight seal), one of several fabrication or assembly techniques or methods may be suitable, depending primarily on the material selections for the component parts and secondarily on the shape and size of the component parts. One connection, joining or attachment approach is to use an adhesive so as to bond one component part to the other(s). Preferably, the selected adhesive is a medical grade adhesive and the approach or technique may include the use of UV light to initiate cross-linking. Another approach, primarily with plastics, is to use ultrasonic welding for fusing together the two component parts. When some other connection, joining or attachment approach is selected or preferred, and is beyond the scope of the options outlined above, that approach is described herein such as the use of an interference fit or the use of threaded fasteners. All fasteners and metal hardware used in the exemplary embodiment are made from a biocompatible, stainless steel alloy.

Figure 16:
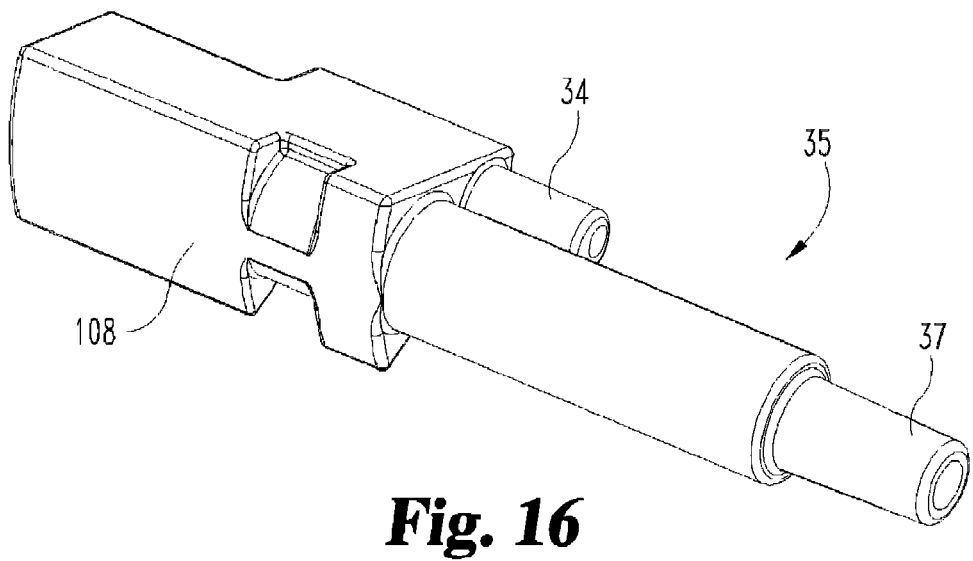
FIG. 16 is a front perspective view of a injection barrel which is one component part of the FIG. 1 injection device.
Figure 16A:
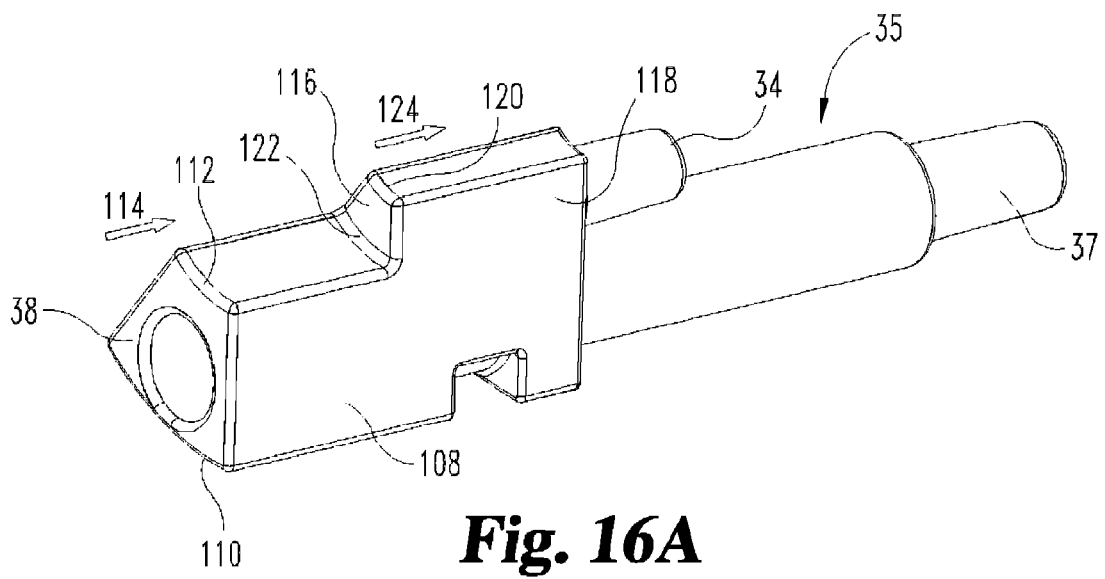
FIG. 16A is a rear perspective view of the FIG. 16 injection barrel.
Figure 16B:
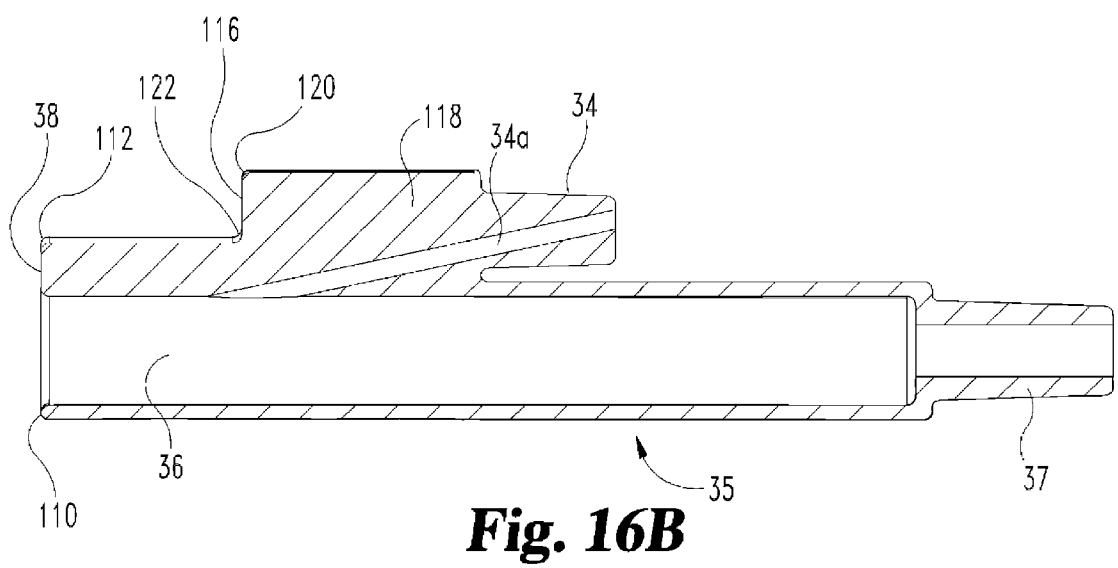
FIG. 16B is a side elevational view, in full section, of the FIG. 16 injection barrel.

As the plunger 30 is depressed, the medicant flows first in a single stream into the manifold hub 29 and then divides into nine (9) similar flow paths for filling the medicant chamber 36 of each barrel 35, see FIGS. 16, 16A and 16B. The distal end of chamber 36 is open at tip 37 and the opposite, proximal end 38 is open but will be closed off by the insertion of one (1) of nine (9) individual plungers 39a of the nine (9) plunger array 39 (see FIGS. 20 and 20A). The tip of each plunger 39a receives an elastomeric seal or sealing piston 168. Each one (1) of the nine (9) injection needles 44 is securely connected with the injection tip 37 of a corresponding one (1) of the nine (9) barrels 35. The proximal end of each needle is media-blasted in order to roughen its outer surface. This proximal end of each needle 44 is then inserted into a corresponding injection tip 37 and the injection tip 37 and needle 44 are bonded together with a medical-grade adhesive which uses UV light to initiate cross-linking resulting in a secure and leak-free connection. The needles 44 extend through multi-lumen shaft 40 and then into tip 42.

As each medicant chamber 36 is filled, the medicant 24 is able to flow out through its corresponding injection needle 44. This flow logically only occurs when the chamber is filled as the path of least resistance for the excess medicant 24 is through the corresponding injection needle 44. With the pointed end (i.e. the open tip 44a) of each of the nine (9) needles 44 extended beyond the multi-lumen tip 42, having full barrels 35 and full needles 44 is shown by the excess flow of medicant droplets coming out of the open tip 44a of one (1) or more of the needles 44. The direction of the falling droplets (see FIG. 7) is representative of pointing device 20 and corresponding tip 42 in an upward direction to ensure full filling of each barrel 35 before droplets appear.

Figure 19:
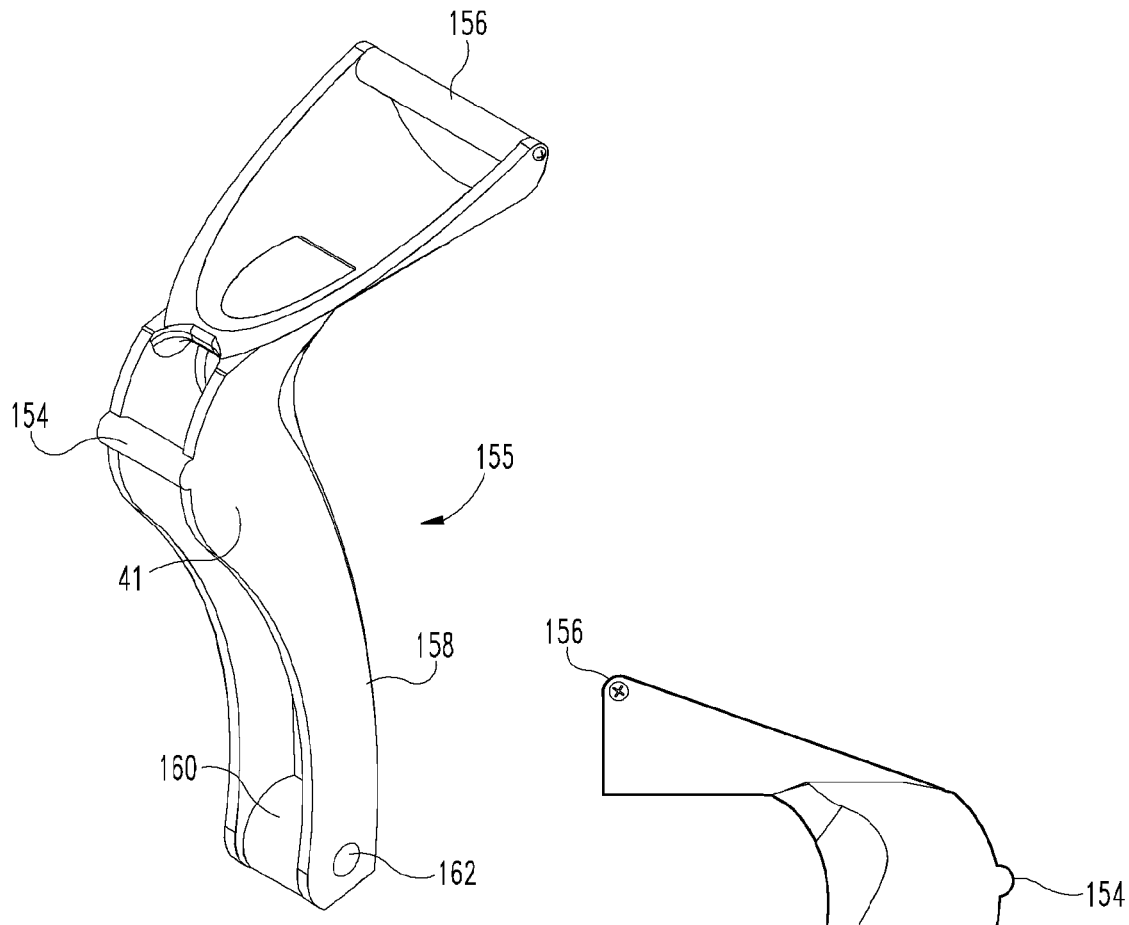
FIG. 19 is a perspective view of a lever which is one component part of the FIG. 1 injection device.
Figure 19A:
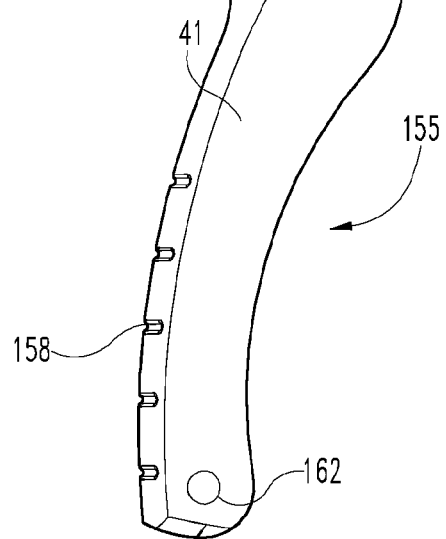
FIG. 19A is a right side elevational view of the FIG. 19 lever.

The next initial preparation step before positioning multi-lumen tip 42 at the treatment site within the patient is to move lever 41 forward (see FIGS. 19 and 19A). This lever movement results in forward movement of the nine (9) plunger array 39. As will be described in greater detail later in this disclosure, the plunger 39a corresponding to each barrel 35 moves forward and closes off the reverse flow path back into delivery syringe 22 via filling tip 34 and filling passage 34a. Slight further advancing of the array 39 purges any excess air which may be found in the nine (9) medicant flow paths from chamber 36 to the open tip 44a of the corresponding needle 44. An essentially complete purge of air is shown, again, by the discharge of medicant droplets from the open tips 44a of the needles 44. The plungers need to then be advanced to a known position (detent or marked increments) corresponding to the correct dosage for the treatment. At the very least the plunger position needs to be noted so that a known dosage is injected. A clear housing or window over the syringe barrels are other options. The needle tips 44a are then withdrawn (i.e. retracted) into multi-lumen tip 42 and device 20 is now ready for use. The remaining steps are to position the tip 42 at the treatment site, deploy or advance the tip of each needle so as to extend those pointed, open tips 44a into the corresponding tissue sites. With each needle tip inserted into the corresponding tissue site, the lever 41 is again used to move plunger array 39 forward so as to dispense at least a portion of the medicant in each chamber 36 into the tissue at the corresponding tissue site. Preferably the entirety of each chamber 36 is emptied.

Figure 3:
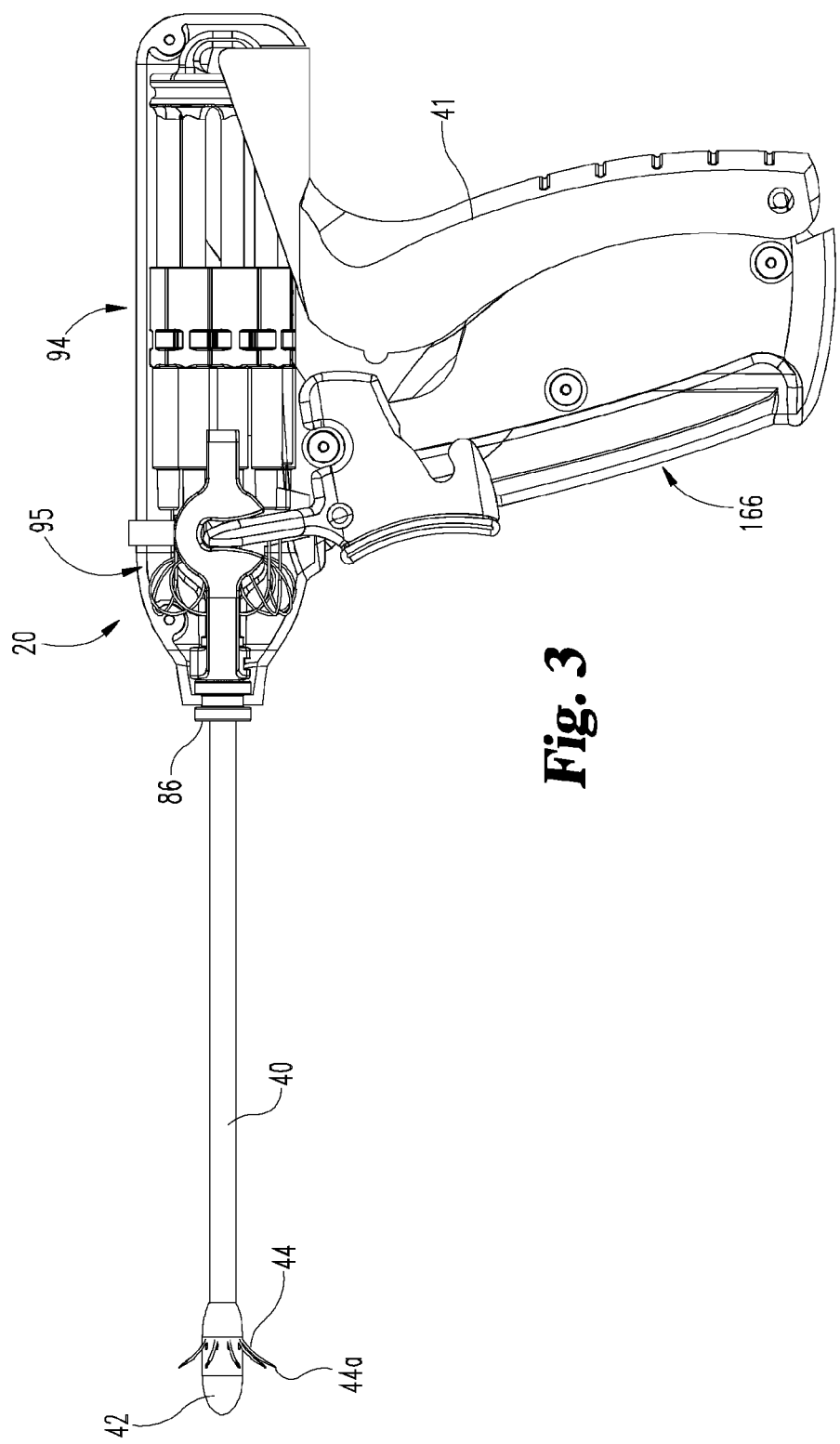
FIG. 3 is a left side elevational view of the FIG. 1 injection device.
Figure 3A:
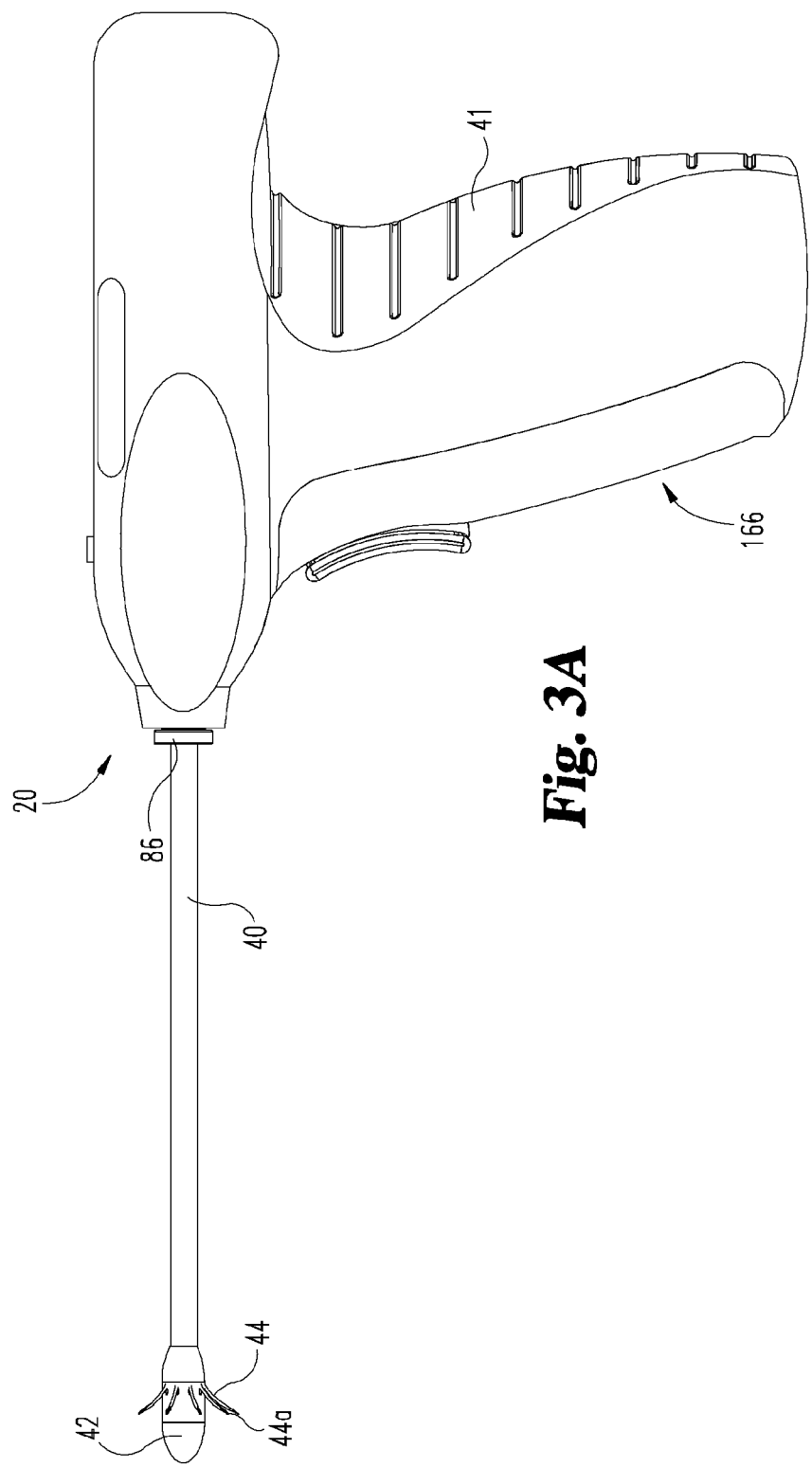
FIG. 3A is a left side elevational view of the FIG. 1A injection device.
Figure 4:
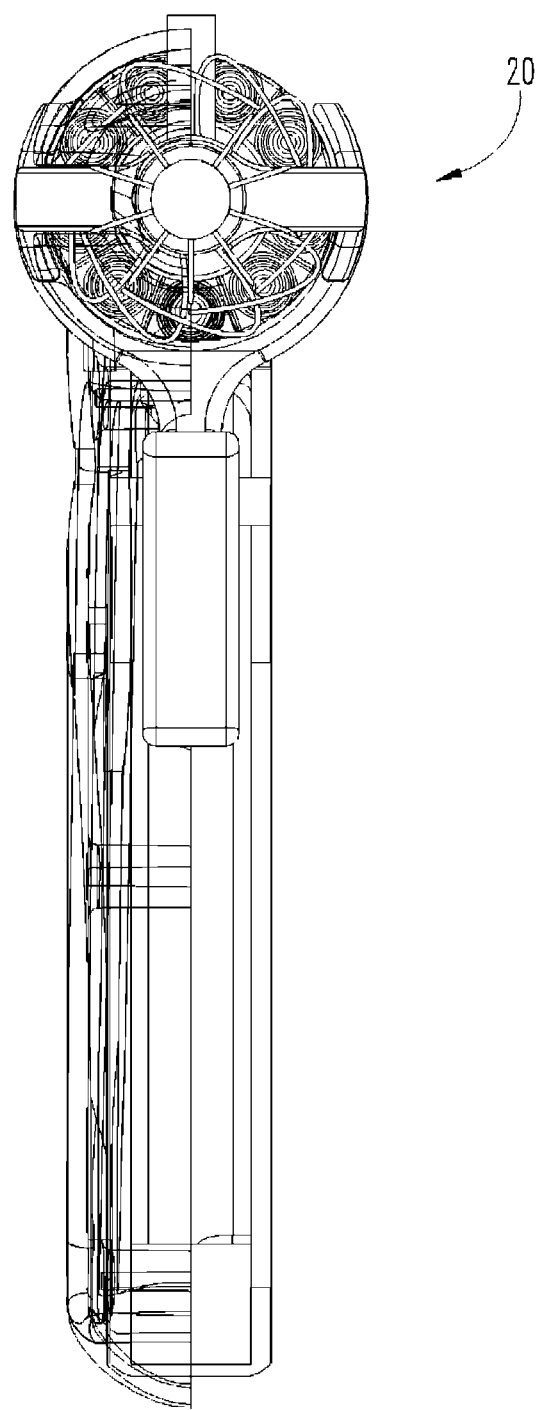
FIG. 4 is a front elevational view of the FIG. 1 injection device, corresponding to a view from the distal end.
Figure 4A:
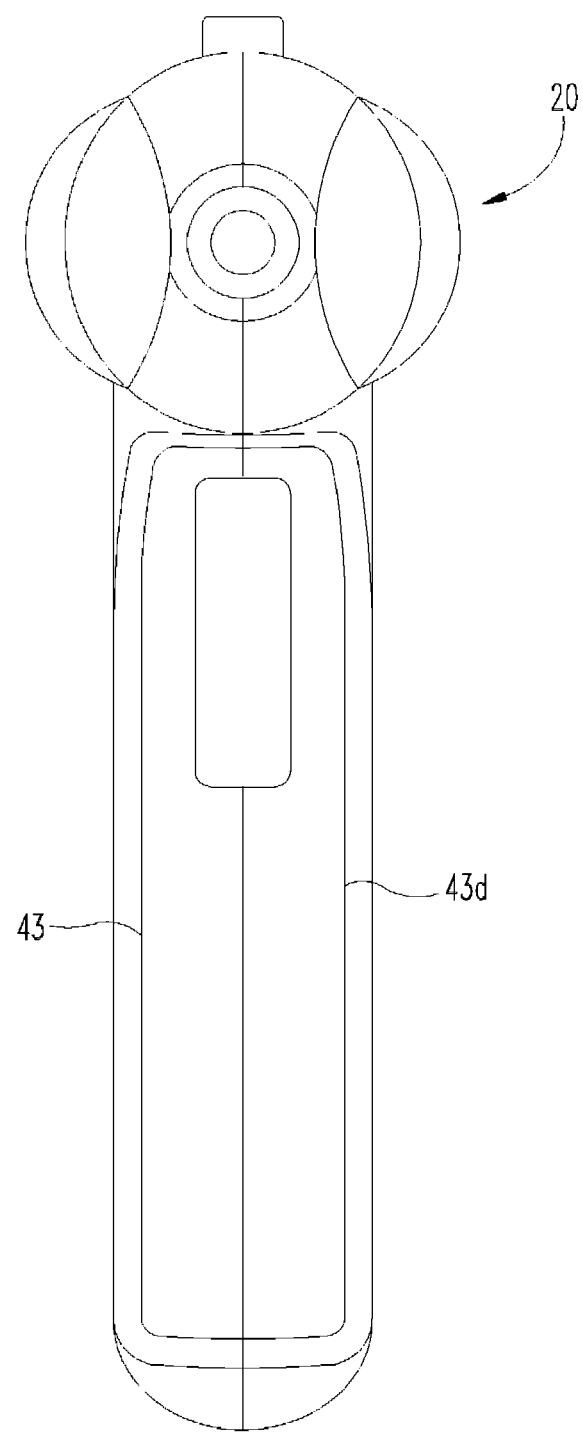
FIG. 4A is a front elevational view of the FIG. 1A injection device, corresponding to a view from the distal end.
Figure 5:
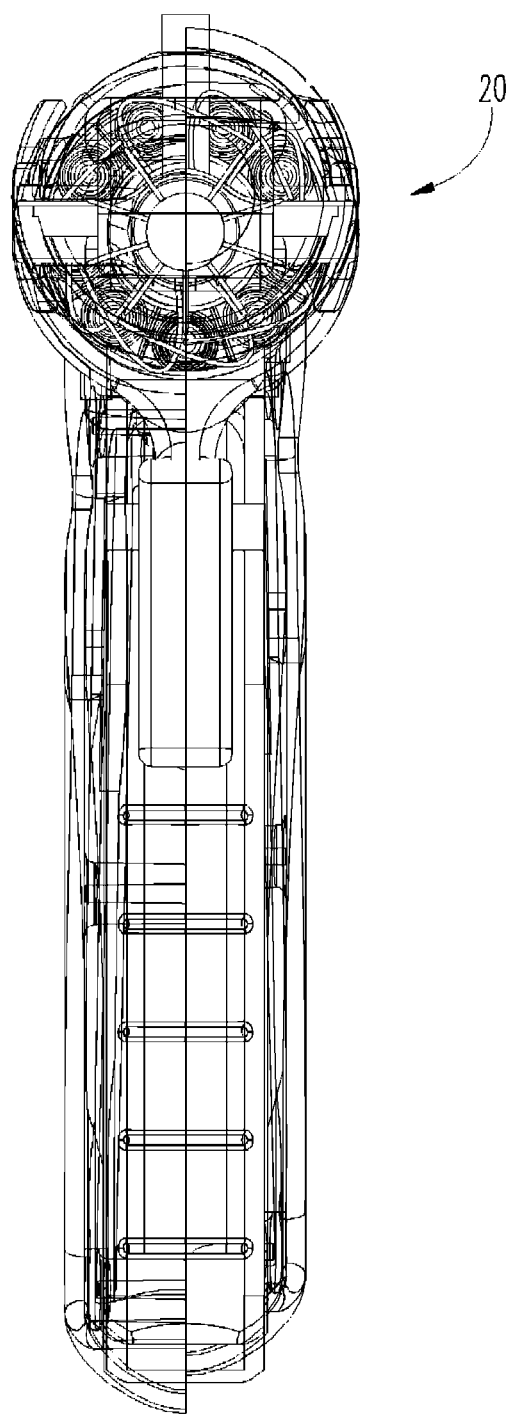
FIG. 5 is a rear elevational view of the FIG. 1 injection device, corresponding to a view from the proximal end.
Figure 5A:
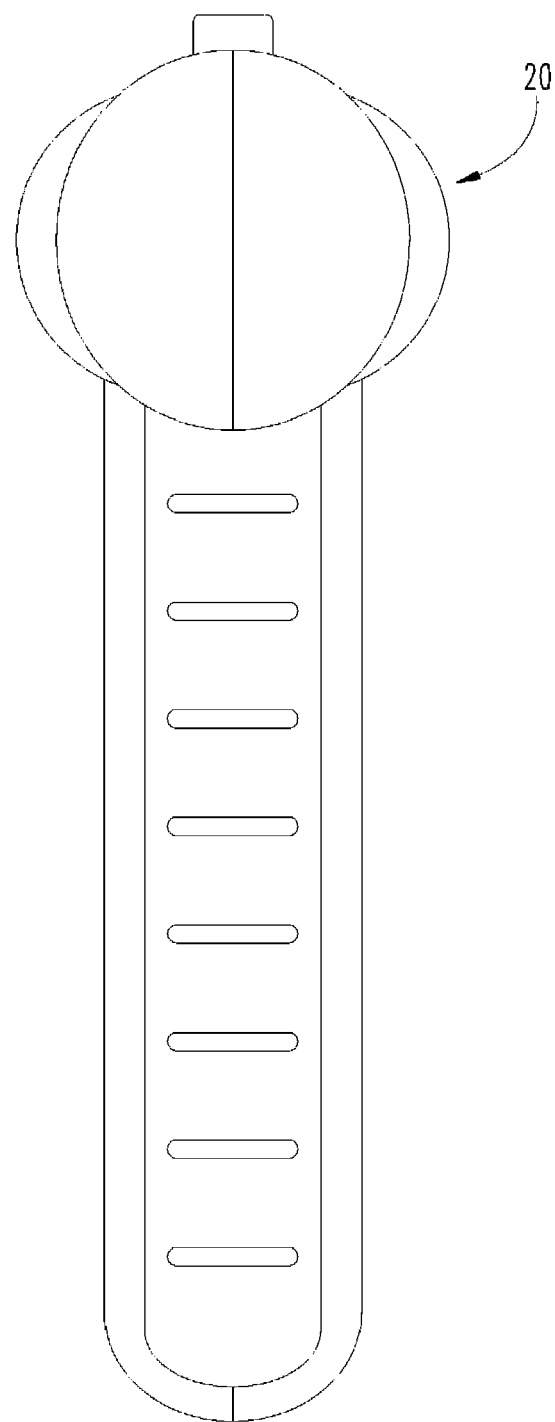
FIG. 5A is a rear elevational view of the FIG. 1A injection device, corresponding to a view from the proximal end.
Figure 6:
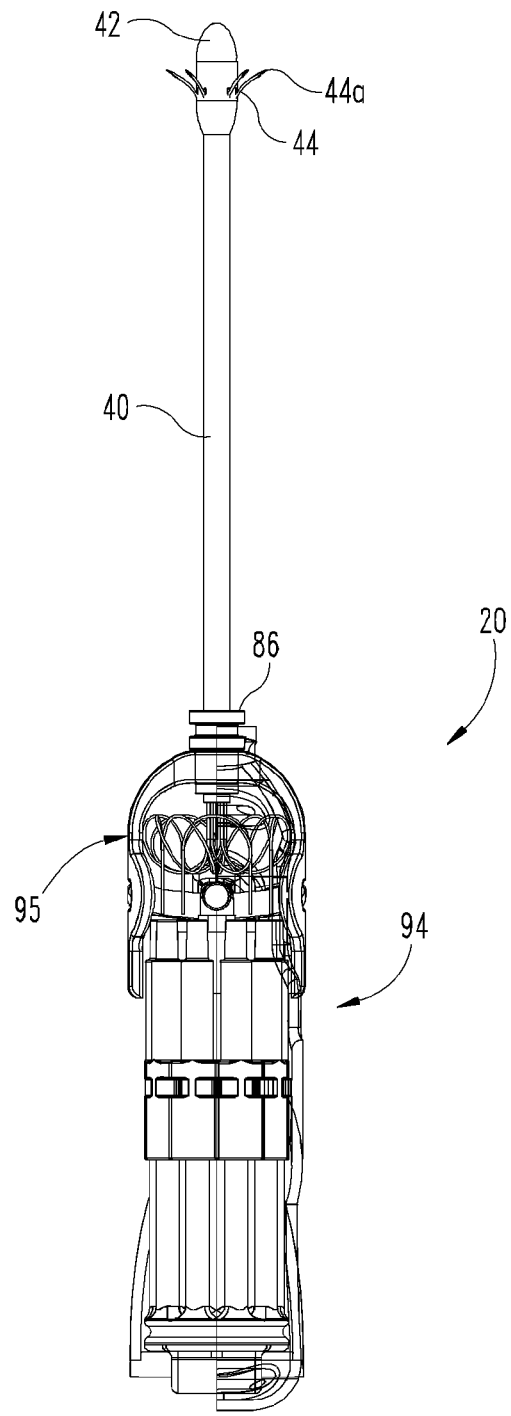
FIG. 6 is a top plan view of the FIG. 1 injection device.
Figure 6A:
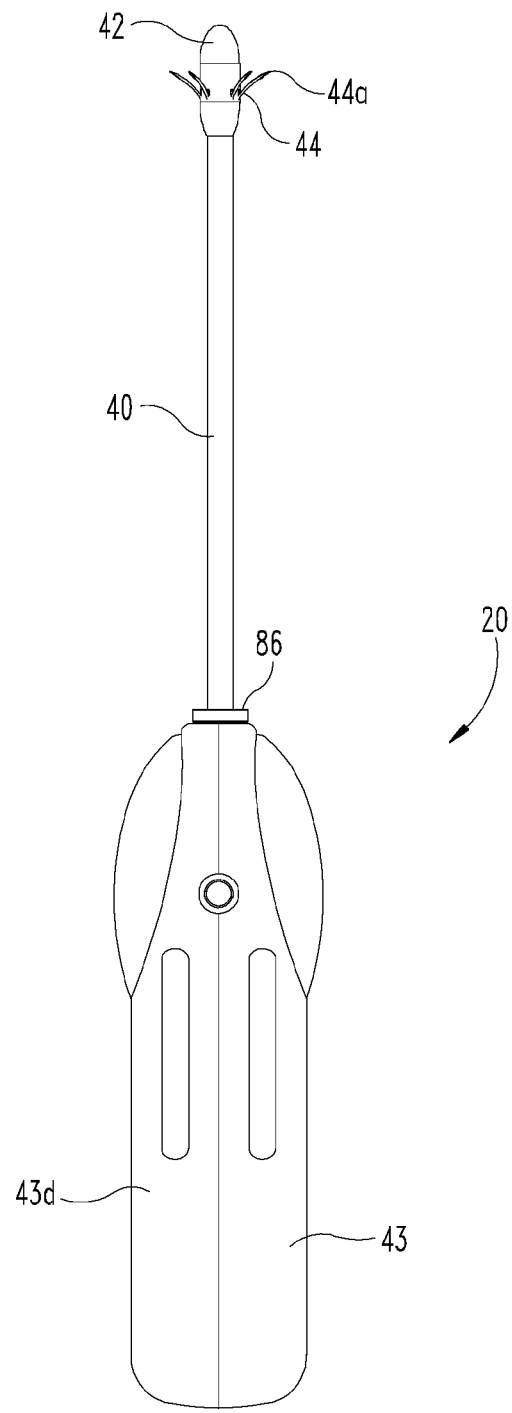
FIG. 6A is a top plan view of the FIG. 1A injection device.

The exemplary embodiment of device 20 is directed at use in conjunction with the treatment of stress urinary incontinence (SUI). The treatment procedure preferably includes nine (9) tissue sites for injection of the selected medicant. For this exemplary treatment, nine (9) injection needles are used and accordingly there are nine (9) barrels 35 and plunger array 39 includes nine (9) individual plungers 39a all part of an integral unit. The nine (9) barrels 35 are ganged together into an array subassembly. Design logic and uniformity suggests that the nine (9) barrels be arranged in an equally-spaced, cylindrical array similar to the cylinder of a pistol. This is illustrated in FIGS. 1-3 and in the design of plunger array 39, the assembly of the barrels 35 and the design of the manifold hub 29.

When the tip 42 of device 20 is positioned at the meatus of the urinary sphincter, there is a further consideration and this is why the "12 o'clock" position does not have a corresponding needle 44. This further consideration is due to the location of sensitive nerves which are to be avoided by the needles.

As should be understood, if device 20 or some variation of device 20 is to be used for some other treatment and/or for some other sphincter, for example, then the number of needles might change. It is also envisioned that the size of device 20 might change as the number of required needles increases or decreases. The arrangement, spacing and pattern of the needles at tip 42 may also change depending on the tissue sites and the desired treatment. All of these variables and variations are contemplated within the scope of the present disclosure.

Figure 7:
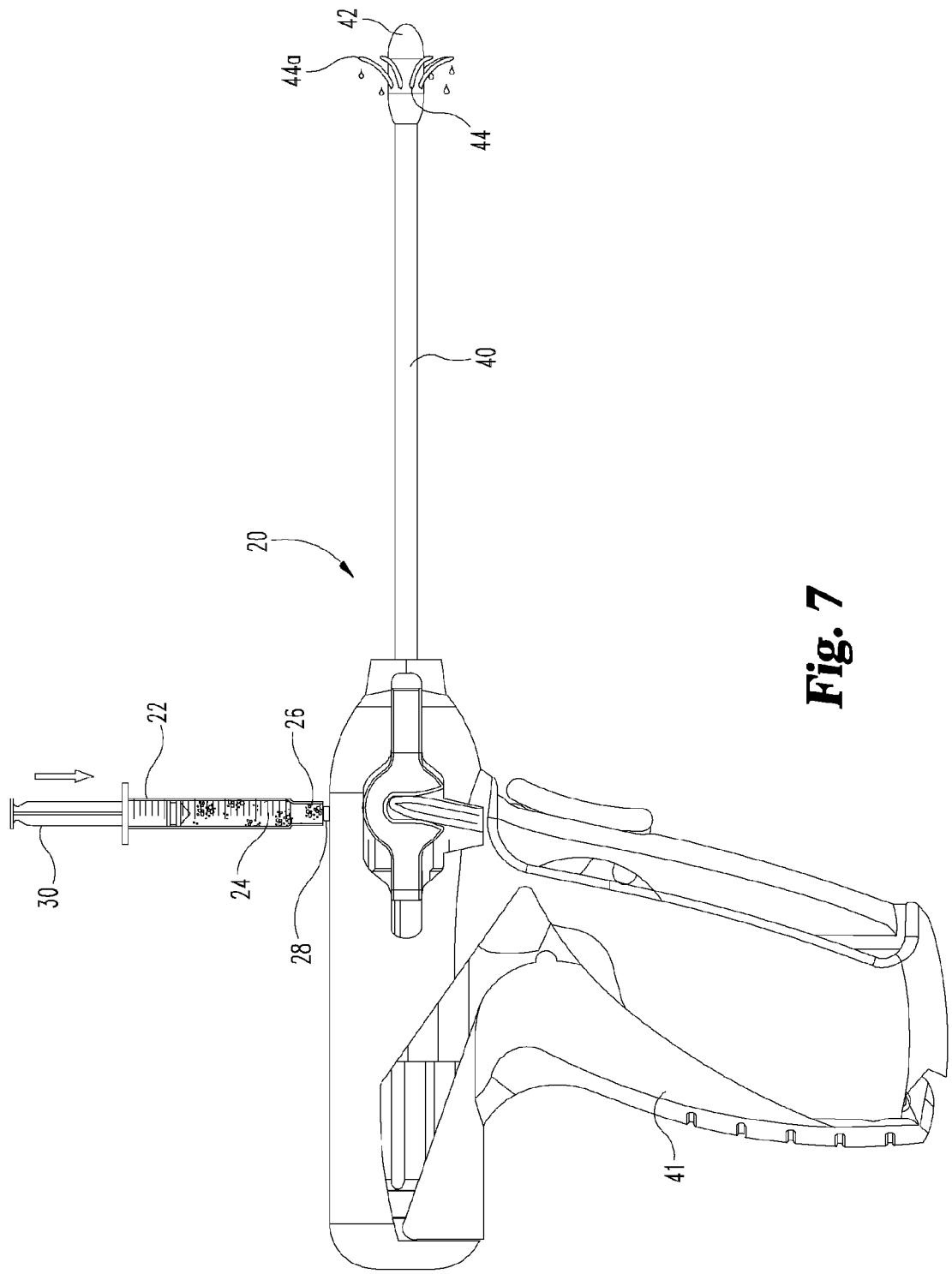
FIG. 7 is a diagrammatic, right side elevational view of an injection system which includes the FIG. 1 injection device.
Figure 8:
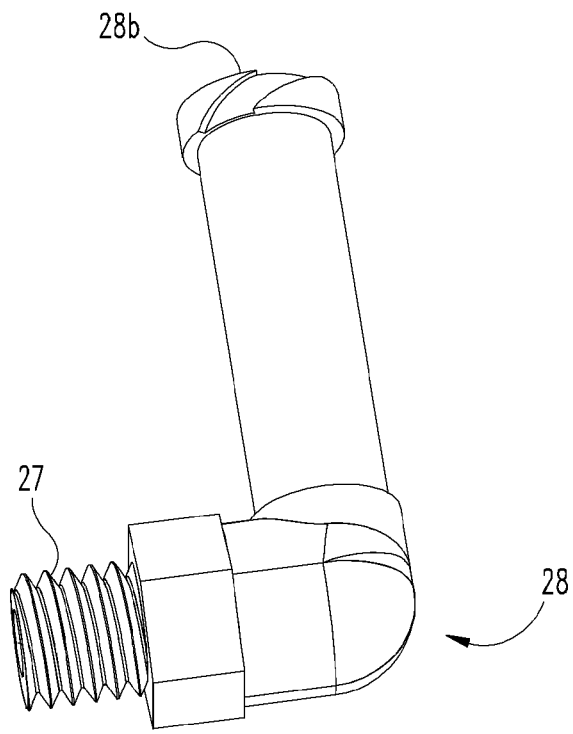
FIG. 8 is a perspective view of an L-shaped adapter which is one component part of the FIG. 1 injection device.
Figure 8A:
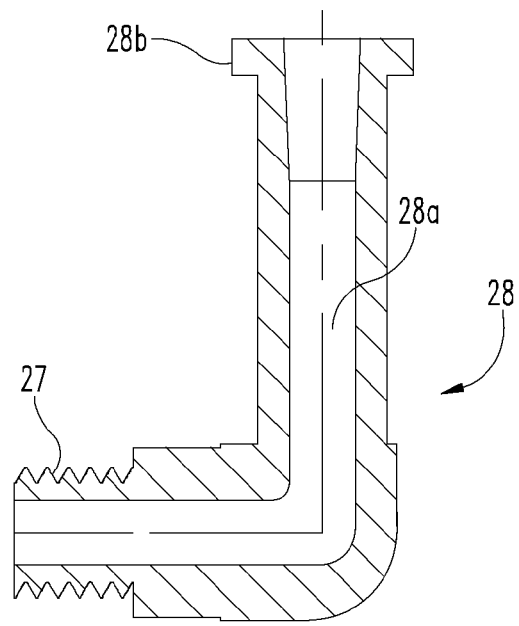
FIG. 8A is a side elevational view, in full section, of the FIG. 8 L-shaped adapter.
Figure 9:
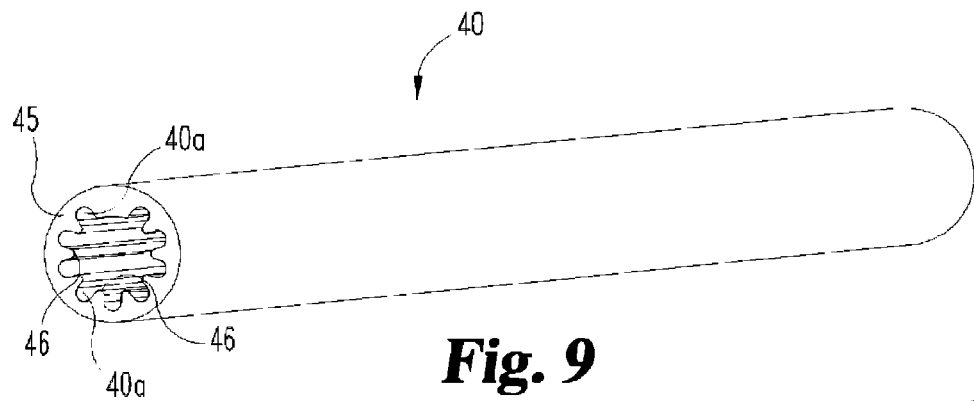
FIG. 9 is a perspective view of a multi-lumen shaft which is one component part of the FIG. 1 injection device.

It is important to note that the FIG. 7 illustration of device 20 includes a two-part housing or cover. This enclosing housing, see FIGS. 22 and 22A, includes a right-side body 43 and a left-side body 43d which is essentially a mirror image of the right-side body 43. The two (2) body halves create a clam-shell enclosing housing which at least partially encloses the trigger mechanism, the plunger array, the barrels and some of the related components. See FIGS. 1A, 2A, 3A, 4A, 5A and 6A. The hub 86 (see FIG. 13) generally denotes the physical interface of the distal end of housing, including right-side body 43 and left-side body 43d, and the multi-lumen shaft 40. The two (2) body halves 43 and 43d of the enclosing housing are fastened together using suitable fasteners which are known in the art and are arranged so as to extend through a plurality of structural portions, such as bosses 43a as shown in the exemplary embodiment. Bosses 43a are arranged so as to avoid internal features while enhancing the structural integrity of the assembly. The generally cylindrical posts 43b and 43c are used as pivot posts for the trigger 98 and for the lever 39, respectively.

Figure 22:
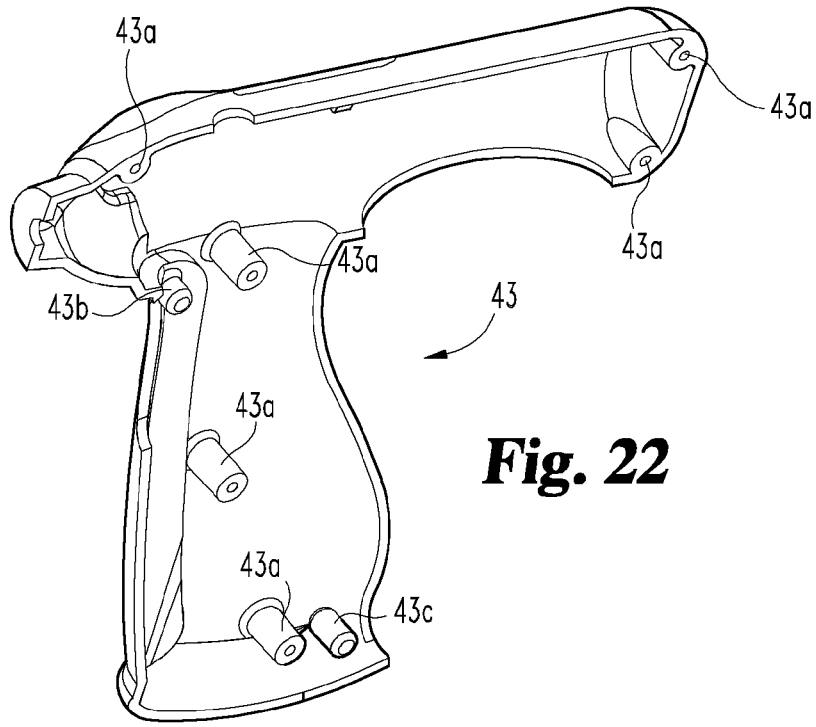
FIG. 22 is a perspective view of one housing half (the right side) which is one component part of the FIG. 1 injection device, the left side housing half being a mirror image.
Figure 22A:
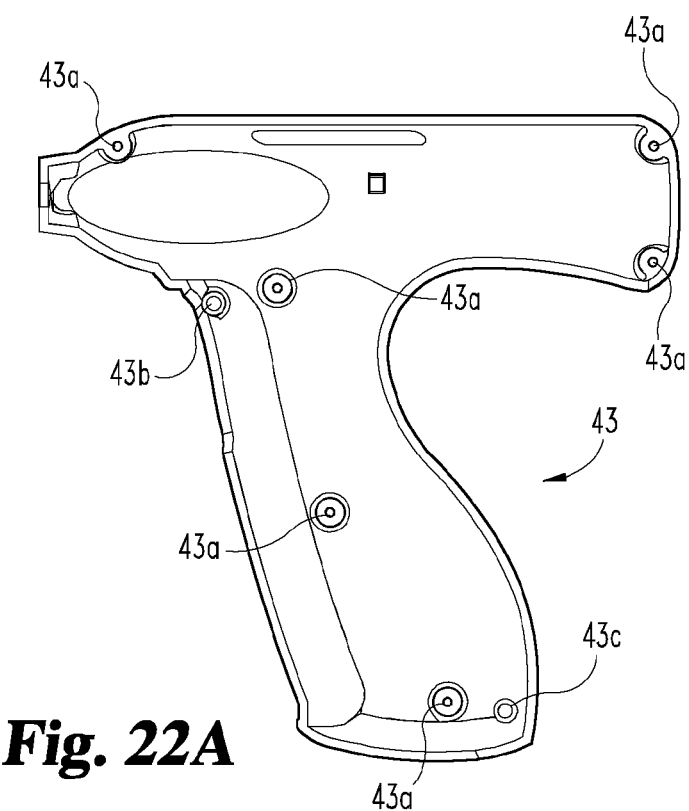
FIG. 22A is a side elevational view of the FIG. 22 housing half.

In order to be able to illustrate the internal construction and complexities of device 20, the right-side body 43 of the housing is the only half included in FIGS. 1, 2, 3, 4, 5 and 6. The elected form of illustration for body 43 is in partial form, as a fully transparent component so as not to block or interfere with the illustrations of the other component parts. The full structure of body 43 is shown in FIGS. 22 and 22A. The fully assembled form of device 20 with both housing halves, i.e. body halves 43 and 43d, is shown in FIGS. 1A, 2A, 3A, 4A, 5A and 6A.

With continued reference to FIGS. 1-6A, it is assumed that all of the component parts are properly configured and assembled, the housing halves which enclose the other component parts are properly shaped, assembled and fastened together. A charge of medicant 24 has been injected into device 20, each barrel 35 is filled with medicant and any residual air in any of the needles 44 has been purged. The delivery syringe 22 has been removed and the small closing cap (or plug) has been connected. Although FIGS. 1-6A illustrate device 20 with the tips 44a of the needles 44 extending out of tip 42, the starting form of device 20 for placement within the patient is with the tips of the needles withdrawn or retracted into tip 42. In this form, the tip 42 is able to be positioned at the desired treatment site without the needles interfering with the desired movement and positioning of device 20.

One advantage of device 20 is the ability to make all of the desired tissue site injections with a single positioning of tip 42. This eliminates any need to turn or rotate tip 42 and/or reposition the tip in another orientation for a second and then a third injection cycle. In the exemplary embodiment of device 20, the nine (9) injection needles 44 are suitable in number and spacing for injections at nine (9) tissue sites into the urinary sphincter of the patient. The reference to nine (9) tissue sites is considered preferred as the example selected for the exemplary embodiment. This is a number which corresponds to the number of injection needles 44. Different treatments and/or different sphincter sites might require a greater number of needles or a fewer number of needles, but regardless, device 20 is able to be modified accordingly consistent with what is provided and what is contemplated by the disclosed embodiments and treatment method.

A single treatment cycle with device 20 means that each needle 44 makes its medicant injection into its corresponding tissue site at a essentially the same time. Each barrel 35 has its own charge of medicant 24 and its own cooperating plunger 39a and sealing piston 168. Further, due to the essentially identical construction of each of the nine (9) barrels 35, the medicant chamber 36 of each barrel holds essentially an identical amount or volume of medicant. As such, each tissue site receives essentially the same amount of medicant regardless of variations in tissue density or other variables. Prior art devices which use a single plunger for a plurality of barrels, via a manifold structure, are unable to address variations in the tissue characteristics such that each site receives an equal amount of injected medicant. With prior art devices, if one (1) tissue site has a higher or greater density of tissue, then based on the principal of the path of least resistance, the other sites will receive an increased dosage of medicant while the site with the greater tissue density will receive less medicant. This problem is solved by the disclosed embodiment. The construction of device 20 also allows an efficient air purge through each needle 44 and eliminates some of the fluid turbulence issues with earlier constructions. As noted regarding some of the earlier constructions, when a single plunger is used to push manifold fluid into a plurality of connected conduits, such as a plurality of barrels which communicate with a single manifold, fluid turbulence can occur.

With continued reference to FIGS. 1-6A, device 20 includes a number of unique component parts which are cooperatively assembled into the illustrated configuration of device 20. The component parts which comprise device 20 are illustrated and described in functional groups beginning with the distal portion. Due to the cooperative relationship between all components there is no rigid boundary line as far as where one portion ends and another begins. Instead, this disclosure selects a few of the components at a time in order to describe their function, structure and cooperative relationship to other components or device 20.

The distal portion of device 20 includes multi-lumen shaft 40 which is assembled into a multi-lumen tip 42. This combination of shaft 40 and tip 42 receives nine (9) curled injection needles 44 which are used as part of the exemplary embodiment of device 20 and are used for the corresponding treatment method. The multi-lumen shaft 40 is a longitudinal or elongated member which includes an outer, generally cylindrical sleeve portion with interior ribs shaped with a fluted configuration, as is illustrated. Shaft 40 is a single-piece, unitary component including the sleeve portion 45 and the nine (9) interior ribs 46. Shaft 40 is preferably made out of a polymeric material, and preferably fabricated by an extrusion process. The nine recessed channels 40a are defined by and between each rib 46. Each channel 40a is constructed and arranged to receive a portion of each needle 44. With each needle 44 fitted into its corresponding channel 40a for the full length of shaft 40, a generally cylindrical rod 47 is inserted into the remaining hollow interior of shaft 40, extending through at least a portion of the overall length of shaft 40. Rod 47 helps to retain each needle 44 in its corresponding channel 40a during use of device 20, without misalignment and/or buckling of any needle 44. Rod 47 is preferably sized to extend from a distal location within tip 42 to a proximal location adjacent multi-lumen ring 88. This "adjacent" location includes a proximal location wherein rod 47 extends into at least a portion of the axial length of ring 88. The annular size of each channel 40a, in lateral cross section, is large enough relative to the diameter size of its corresponding needle 44 to permit each needle to freely slide through its corresponding channel 40a as part of the deployment of the tip 44a of each needle out of tip 42.

Figure 10:
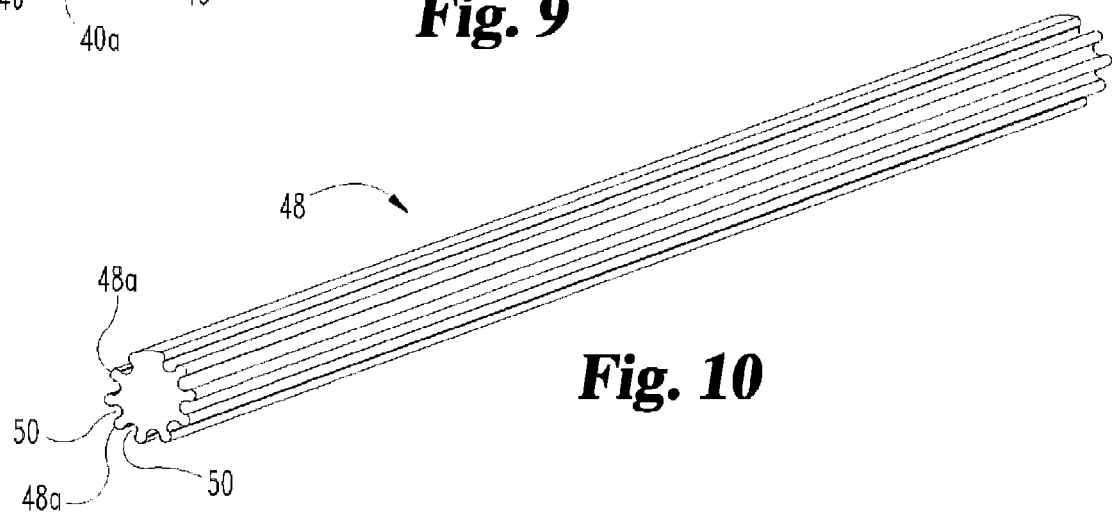
FIG. 10 is a perspective view of a multi-lumen shaft which is an optional second embodiment for the style of shaft of FIG. 9.
Figure 11:
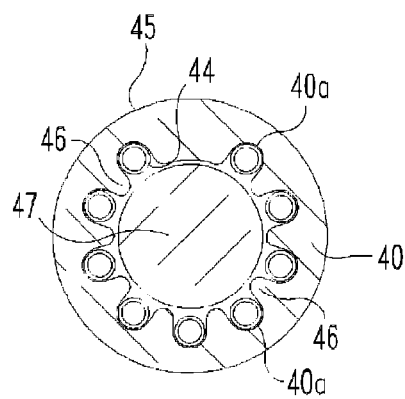
FIG. 11 is an end elevational view, in full section, of the FIG. 9 multi-lumen shaft with nine (9) injection needles loaded therein and an internal support rod.
Figure 11A:
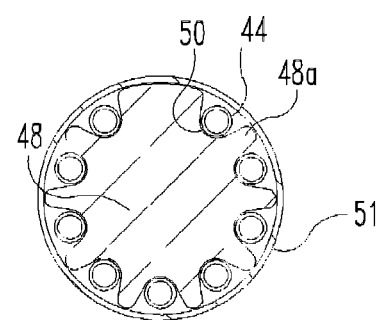
FIG. 11A is an end elevational view, and full section, of the FIG. 10 multi-lumen shaft with nine (9) injection needles loaded therein and an external support sleeve.

A second embodiment for the multi-lumen structure which is represented by shaft 40 is to use a ribbed rod 48 (see FIG. 10). Whether using the generally cylindrical tube form of shaft 40 for carrying the nine (9) injection needles, or using a ribbed rod 48 for the nine (9) needles, it is to be noted that there is a supporting structure in either of these two (2) embodiments preferably extending from the main body of device 20 to within the location of tip 42. Likewise, whether using shaft 40 or using rod 48, the distal tip of that structure inserts into the open proximal end of tip 42 which is accessible and used for their secure connection. An end section view of the cooperating, generally concentric assembly of needles 44 into shaft 40 is illustrated in FIG. 11. In FIG. 11A, an end section view is provided of the nine (9) needles 44 as they are received by the alternative embodiment using rod 48. Rod 48 is a single-piece, unitary component which is preferably fabricated by an extrusion process from a polymeric material. Rod 48 defines nine (9) ribs 48a and in alternating sequence with each rib 48a is a recessed channel 50. Each channel 50 is constructed and arranged to receive a corresponding needle 44. In order to help secure each needle 44 in its corresponding channel 50, a thin sleeve 51 is slipped over the needle-loaded rod 48, see FIG. 11A. Sleeve 51 helps to retain each needle 44 in its corresponding channel 50 during use of device 20 in this second embodiment, without misalignment and/or buckling of any needle 44. Sleeve 51 is preferably sized to extend from a distal location within tip 42 to a proximal location adjacent the distal face of multi-lumen ring 88. The annular size of each channel 50, in lateral cross section, is large enough relative to the diameter size of its corresponding needle 44 to permit each needle to free slide through its corresponding channel 50 as part of the deployment of the tip 44a of each needle out of tip 42.

Whichever embodiment is selected as part of device 20, each of the nine (9) needles are able to move freely within the selected carrier, whether within shaft 40 or around rod 48 so as to be extendable (i.e. deployed) out of openings in tip 42 or retracted back into tip 42. The ribbed or fluted designs for these two (2) support members, whether shaft 40 or rod 48, define nine (9) needle-receiving channels 40a (see shaft 40) or in the alternative embodiment channels 50 for use with rod 48.

Figure 12:
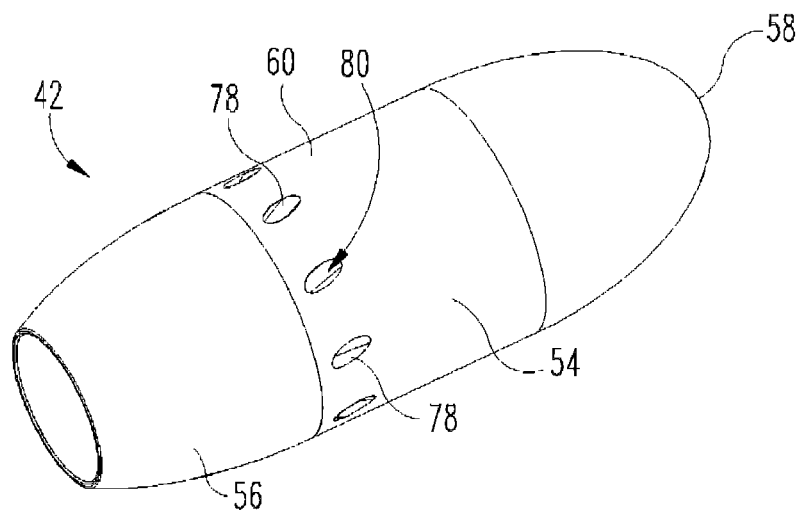
FIG. 12 is a perspective view of a multi-lumen tip which is one component part of the FIG. 1 injection device.
Figure 12A:
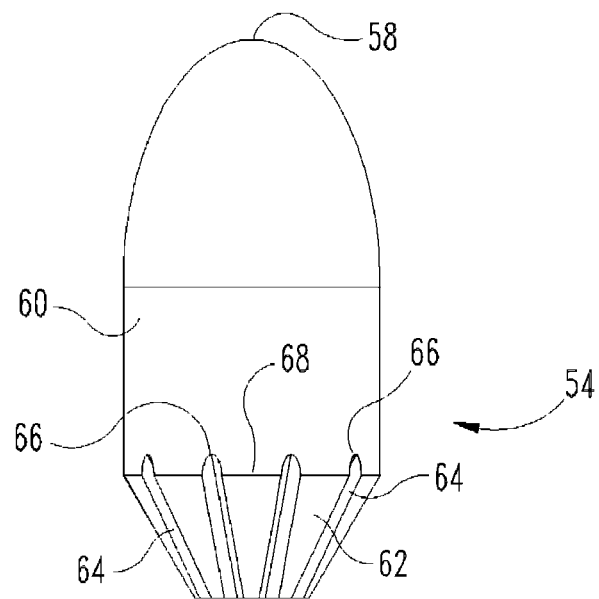
FIG. 12A is a top plan view of a distal portion of the FIG. 12 multi-lumen tip.
Figure 12B:
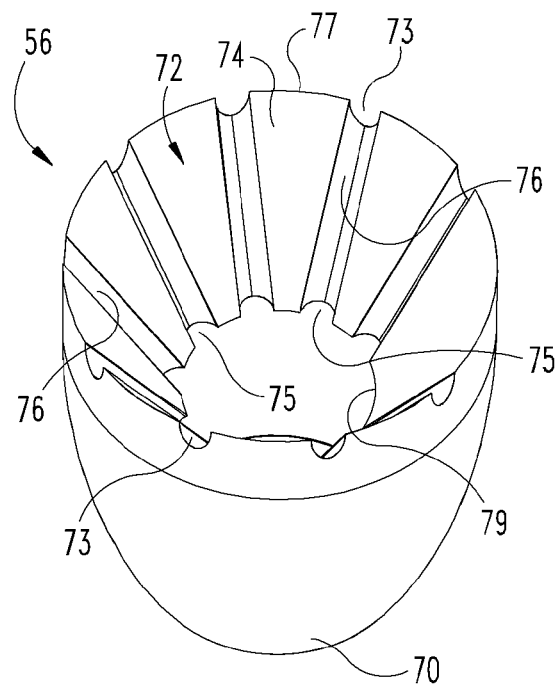
FIG. 12B is a perspective view of a proximal portion of the FIG. 12 multi-lumen tip.
Figure 12C:
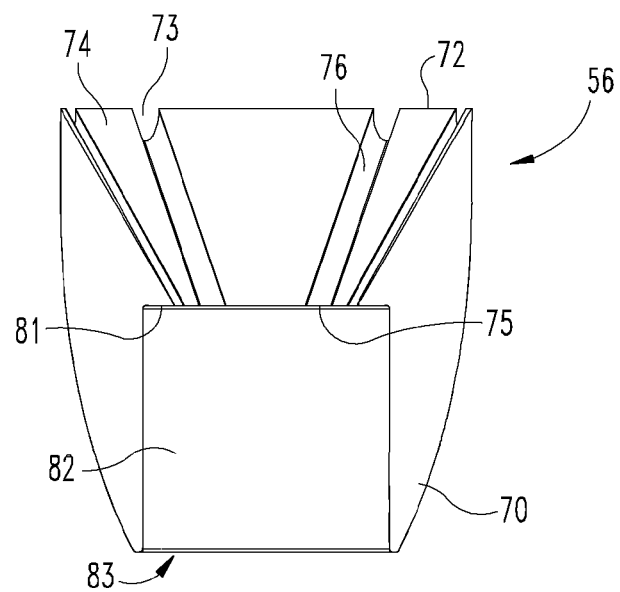
FIG. 12C is a top plan view, in full section, of the FIG. 12B proximal portion.

Multi-lumen tip 42 (see FIG. 12) is preferably a subassembly of two (2) cooperating members, including a distal tip portion 54 (see FIG. 12A) and a proximal tip portion 56 (see FIG. 12B). These two (2) portions 54 and 56 are securely joined together in order to form tip 42. With continued reference to FIGS. 12, 12A and 12B, portion 54 includes a closed, dome-shaped head 58, a generally-cylindrical body 60 and a frustoconical base 62 which defines a pattern of nine (9) generally semi-cylindrical grooves 64. The nine (9) grooves 64 extend the full frustoconical length of base 62 and create break-out apertures 66 adjacent the lower edge 68 of body 60.

With continued reference to FIGS. 12, 12A, 12B and 12C, portion 56 includes an open-tapered proximal end 70 and an opposite end 72 which is shaped with a recessed frustoconical surface 74. Surface 74 defines nine (9) generally semi-cylindrical grooves 76 which are sized, shaped and arranged to cooperate with grooves 64 when the two portions 54 and 56 are securely joined together into tip 42. Grooves 76 extend the full frustoconical length of surface 74 creating break-out edge apertures 73 and 75 which are generally semi-circular or part-oval in shape. Apertures 73 are adjacent outer edge 77 and apertures 75 are adjacent inner edge 79. Inner edge 79 corresponds to surface 81 which is at the distal end of the counterbore 82. Open end 83 receives the distal end of shaft 40. Edge 77 is in tight abutment with edge 68 as portions 54 and 56 are securely joined together. This assembly results in two (2) sets of edge apertures (apertures 66 and 73) combining to cooperatively define the nine (9) needle openings 78 which are shown as being defined by multi-lumen tip 42, see FIG. 12 as an example.

Base 62 fits within the recess of opposite end 72 and abuts up against surface 74 such that grooves 64 and grooves 76 define nine (9) needle-receiving passages 80. These passages 80 begin at the location of surface 81. These passages end at the location of the defined needle openings 78. When multi-lumen shaft 40 and multi-lumen tip 42 are properly assembled and joined together, the nine (9) defined needle channels 40a are aligned with the nine (9) passages 80 which are in communication with the nine (9) needle openings 78. In the alternative embodiment, involving the use of rod 48, its defined needle channels 50 are aligned with the nine (9) passages 80 which are in communication with the nine (9) needle openings 78.

The multi-lumen shaft 40 is sized and shaped to fit closely within counterbore 82 and is securely connected therewith. The cylindrical rod 47 has a sliding fit through the interior of shaft 40 and one way to fix rod 47 in position and one way to fix the relationship between rod 47 and sleeve 40 is to securely attach the end of rod 47 to the center portion of surface 81. The connection of rod 47 to surface 81 still leaves open the proximal entrance to each passage for receipt of a corresponding needle.

Figure 13:
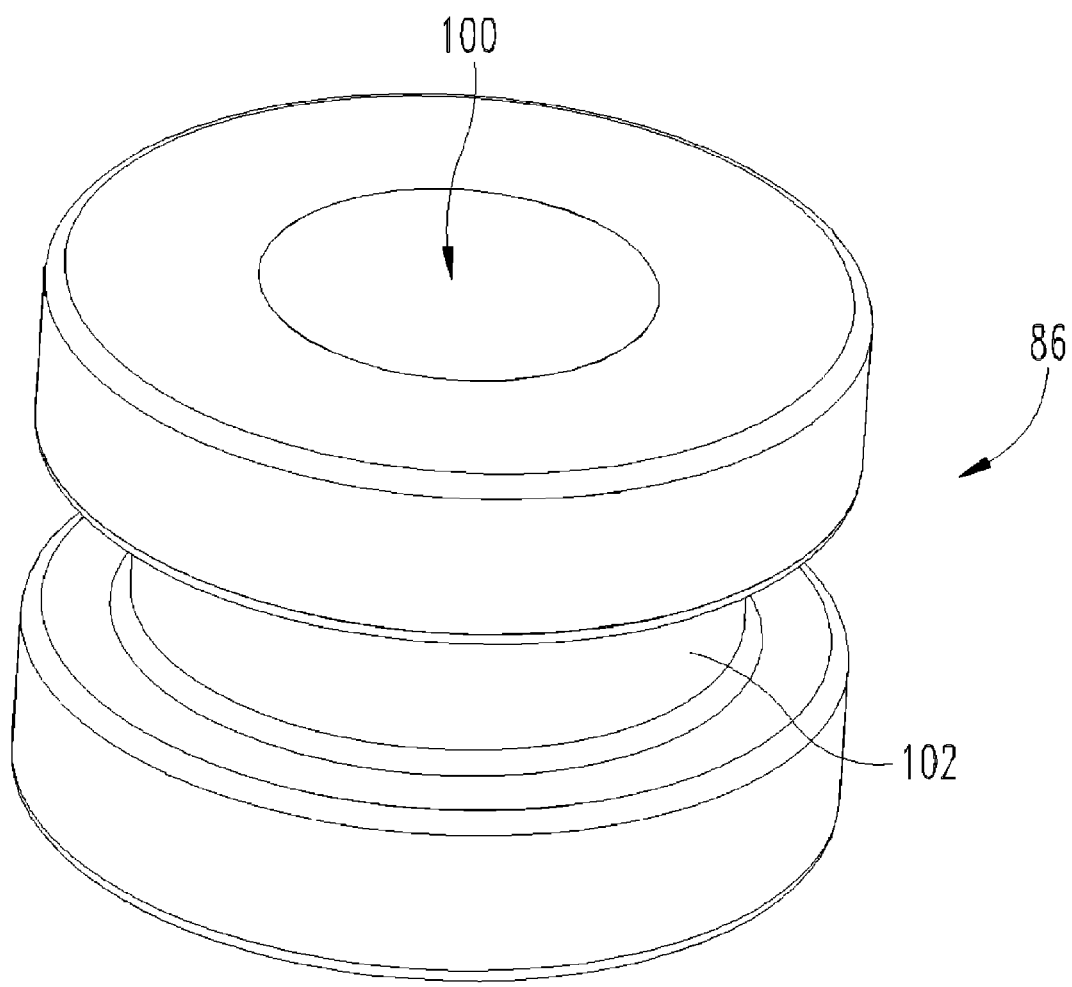
FIG. 13 is a perspective view of a hub which is one component part of the FIG. 1 injection device.
Figure 15:
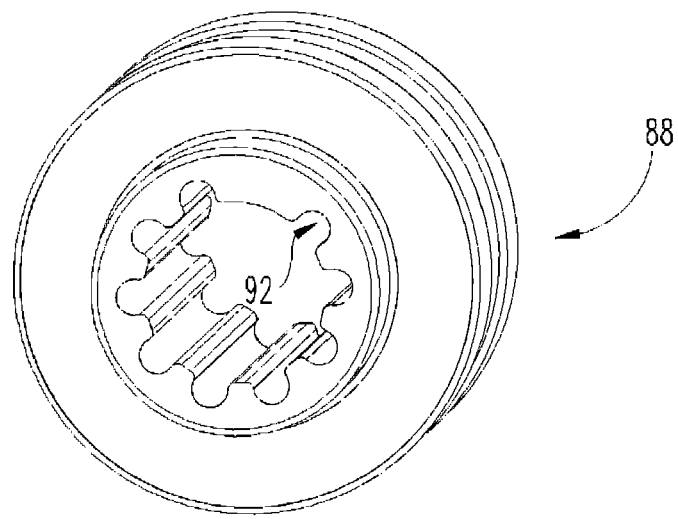
FIG. 15 is a perspective view of a multi-lumen ring which is one component part of the FIG. 1 injection device.
Figure 15A:
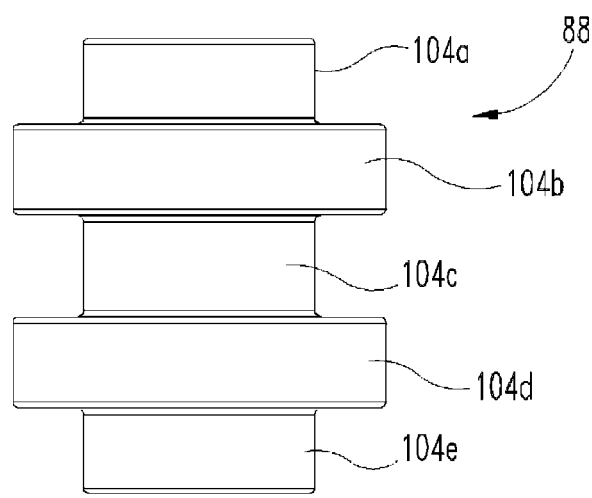
FIG. 15A is a top plan view of the FIG. 15 multi-lumen ring.

With continued reference to FIGS. 1-6A, device 20 further includes a hub 86, a multi-lumen shaft ring 88 and nine (9) barrels 35. The construction of hub 86 is illustrated in FIG. 13. The construction of multi-lumen shaft ring 88 is illustrated in FIGS. 15 and 15A. The construction of each barrel 35 is illustrated in FIGS. 16, 16A and 16B.

Hub 86 is preferably a single-piece, unitary component which is injection molded from a polymeric material, such as polyacetal. Ring 88 is preferably a single-piece, unitary component which is injection molded from a polymeric material. Each barrel 35 is preferably a single-piece, unitary component which is injection molded from a polymeric material, such as polycarbonate or polypropylene.

As illustrated in the assembled configuration of device 20, multi-lumen shaft 40 extends through at least a portion of hub 86. As the proximal ends of the nine (9) needles exit from shaft 40 in the vicinity of hub 86, those nine (9) needles are received by the nine (9) needle-receiving channels 92 which are defined by ring 88. A portion of shaft 40 is securely attached to hub 86 by the use of a suitable adhesive. Preferably cylindrical rod 47 extends into and through ring 88 to help facilitate the initial positioning and retention of the needles 44 within the receiving channels 92 of ring 88. The nine (9) barrels 35 are sized and shaped so as to generally fit together into a generally cylindrical array which is identified herein as the barrel subassembly 94. The distal end of tip 37 of each barrel 35 receives one end of the corresponding curled injection needle 44. The curled portion 44b of each needle 44 is positioned in a clearance space 95 within the housing of device 20. Clearance space 95 is positioned between the barrel subassembly 94 and ring 88. The uncurled, straight portion of each needle 44 which extends from its curled portion 44b to its open pointed tip 44a, extends through a corresponding channel 92 and then through a corresponding channel 40a. In tip 42, each needle 44 extends through a corresponding passage 80. When deployed, the tip of each needle protrudes out of its corresponding opening 78 as is illustrated in FIGS. 1 and 1A.

The portion of each needle 44 which is received by its corresponding channel 92 is securely attached within and to ring 88 using a suitable adhesive. As a result of this secure connection between needles 44 and ring 88, movement of ring 88 causes movement of the nine needles 44. Movement of the needles is required to be able to deploy and retract the needle tips 44a relative to multi-lumen tip 42.

The use of device 20 allows the needles 44 to be moved from a retracted position to an extended or deployed position as noted. In the retracted position the pointed tip 44a of each needle 44 does not protrude out of its corresponding needle opening 78 in tip 42. In the extended position the open pointed tip 44a of each needle 44 is extended out through its corresponding opening 78, into the corresponding and selected tissue site. The tissue sites are not shown in FIG. 1, but it is to be understood that with proper positioning of tip 42, at the meatus of the urinary sphincter in the exemplary embodiment, when the needles 44 are deployed, the pointed tips 44a of those needles extend into the corresponding tissue sites for injection of medicant at each of those tissue sites.

The needles 44 are able to move within channels 40a and within passages 80 relative to their defining structures and as the needles are moved through tip 42, the pointed tip 44a of each needle 44 moves and protrudes out of its corresponding opening 78. Ring 88 is used in order to securely attach onto a portion of each needle so that its pointed tip can be deployed and extended out of its corresponding opening. The attachment between ring 88 and the needles 44 is by the use of a suitable adhesive. Ring 88 is sized and shaped for receipt of the nine (9) needles with one (1) needle each being positioned in each of the nine (9) channels 92 which are defined by ring 88 and which extend the full length of ring 88. There is one (1) needle 44 placed in each channel 92 and each needle is securely bonded in place within ring 88 using a suitable adhesive. In the exemplary embodiment a UV cured adhesive is used to lock together the ring 88 and each of the nine (9) needles 44. A yoke 96 (see FIGS. 17 and 17A) and a trigger 98 (see FIGS. 18 and 18A) combine in a cooperatively arranged manner in order to move ring 88 forward in the direction of tip 42. The movement of ring 88 in a forward direction (toward tip 42) advances each needle 44 in order to deploy the pointed tip 44a of each needle into a corresponding tissue site. The combination of ring 88, yoke 96 and trigger 98 defines the principal components of a control linkage for the deployment of the needle tips.

Referring now to FIG. 13, the details of hub 86 are illustrated. Hub 86 is positioned at the proximal end of multi-lumen shaft 40, adjacent ring 88. Hub 86 is an annular component defining a generally cylindrical, hollow interior 100 which receives a portion of shaft 40. The larger diameter ends of hub 86 define a reduced diameter concentric portion 102 which is centered therebetween. The two (2) halves of the housing including the right half body 43 and its left half which is a mirror image, fit together, clamping around portion 102.

Referring now to FIGS. 15 and 15A, the details of ring 88 are illustrated. Ring 88 defines a hollow interior and five (5) generally concentric annular portions 104a, 104b, 104c, 104d and 104e. Portion 104a corresponds to the distal end of ring 88 in its assembled orientation in device 20 and portion 104e corresponds to the proximal end. The two larger diameter center portions 104b and 104d are used as abutment surfaces for the engaging portions of yoke 96. Other portions of yoke 96 are engaged by portions of trigger 98. As trigger 98 is manipulated in one mode, the yoke 96 is moved forward in a distal direction which advances ring 88 and thus advances the tips 44a of each needle 44 so as to extend outwardly beyond the outer surface of multi-lumen tip 42. The nine (9) elongated channels 92 run substantially parallel to the longitudinal axis of ring 88 and extend the entire axial length of ring 88. Each channel 92 which has an overall shape which is part-cylindrical is sized so as to be able to receive each needle diameter with sufficient space for receipt of an adequate amount of adhesive so as to securely anchor each of the nine (9) needles into ring 88.

Referring now to FIGS. 16, 16A and 16B, the details of barrel 35 are illustrated. In addition to the structural features already described, each barrel 35 includes a body portion 108 which is adjacent the end opposite injection tip 37. This body portion 108 has a sector shape with a curved outer edge 110 and a generally concave curved inner edge 112. The arcuate measurement in degrees is approximately 40 degrees. This means that when all nine (9) barrels 35 are grouped together into a circular array as is illustrated, into the form of barrel subassembly 94, the subassembly form is generally cylindrical. An interior bore or aperture 114, defined by the nine (9) inner edges 112, opens into a shelf 116 defined by the nine (9) raised ribs 118. Each rib 118 has a curved inner edge 120 and a generally concentric curved outer edge 122. Edges 112 and 122 are at opposite ends of the surface defining aperture 114. The cylindrical arrangement of nine (9) inner edges 120 defines a bore 124 which is generally coaxial with the internally threaded bore 126 of hub 29. This construction allows the use of a clamping plate (not illustrated) which is applied against shelf 116 of each of the nine (9) barrels 35 as part of barrel subassembly 94 so as to securely clamp the subassembly 94 against the proximal face of hub 29. This clamping structure helps to maintain the generally cylindrical form of barrel subassembly 94 and keep the tapered fittings seated tightly and/or sealingly connected.

Figure 17:
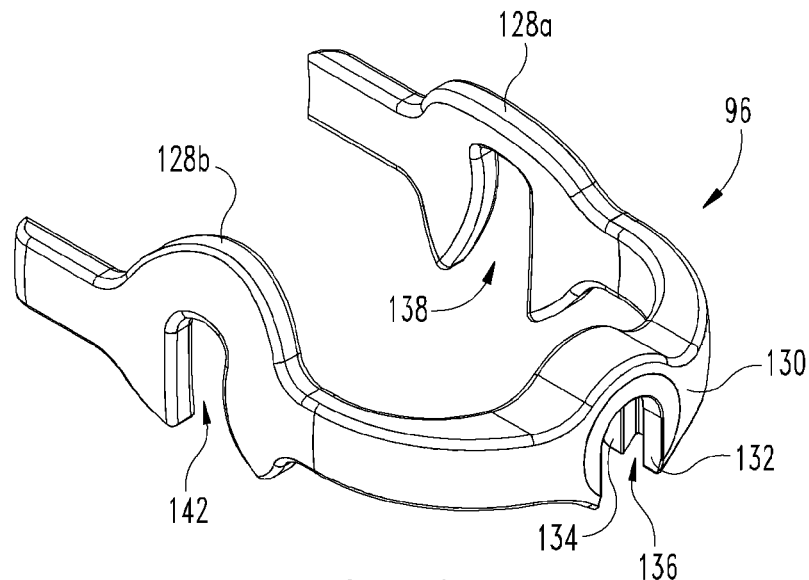
FIG. 17 is a perspective view of a yoke which is one component part of the FIG. 1 injection device.
Figure 17A:
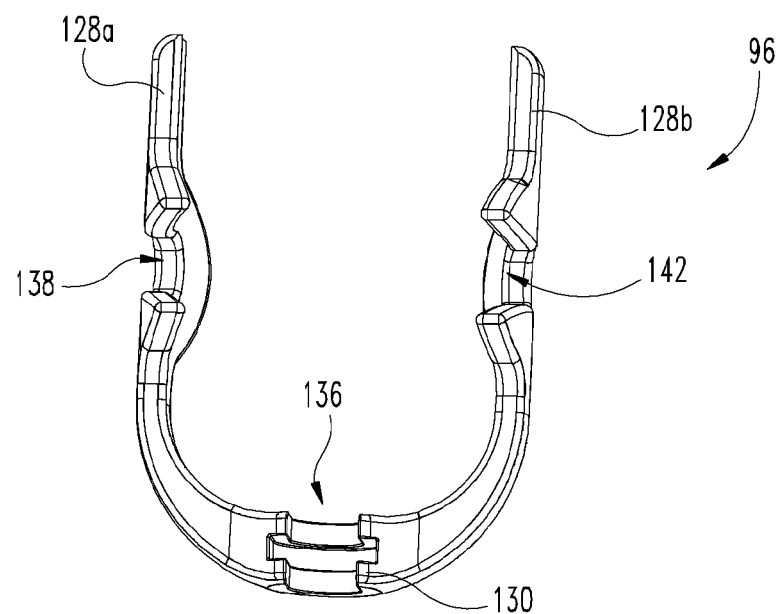
FIG. 17A is a bottom plan view of the FIG. 17 yoke.

Referring to FIGS. 17 and 17A, but details of yoke 96 are illustrated. Yoke 96, is preferably a single-piece, unitary component which is injection molded from a polymeric material, such as nylon. Yoke 96 includes two (2) arm portions 128a and 128b integrally extending into a distal hub 130. Hub 130 is constructed and arranged with two (2) spaced apart wall portions 132 and 134. These two (2) wall portions define a clearance space 136 therebetween. This clearance space 136 is sized and shaped so as to fit down over annular portion 104b of ring 88. Similarly, wall portion 132 fits over portion 104a of ring 88 and wall portion 134 fits over portion 104c.

Arm portion 128a defines a slot 138 which receives a clevis-type arm 140 of trigger 98. Arm portion 128b defines a slot 142 which receives another clevis-type arm 144 of trigger 98. When the trigger is squeezed and pivots about pivot post 43b, arms 140 and 144 act against abutment surfaces which partially define slots 138 and 142, respectively, so as to advance yoke 96 in the direction of tip 42. This movement of yoke 96 causes advancing movement of ring 88 and thereby advancing movement for each needle 44 which is securely retained and captured within ring 88. Slot 138 is defined by one (1) curved wall and by one (1) substantially flat wall. Slot 142 is defined by one (1) curved wall and by one (1) substantially flat wall.

Figure 18:
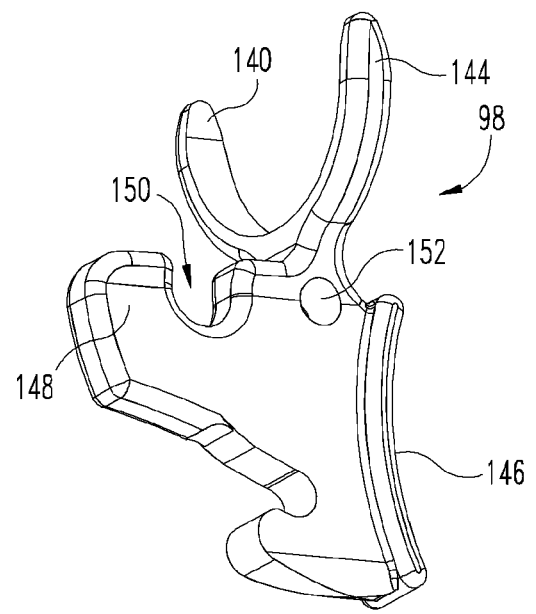
FIG. 18 is a perspective view of a trigger which is one component part of the FIG. 1 injection device.
Figure 18A:
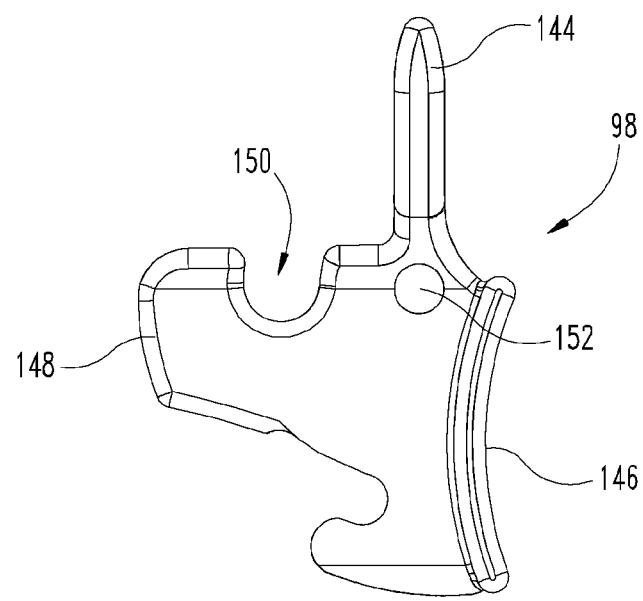
FIG. 18A is a right side elevational view of the FIG. 18 trigger.

Referring to FIGS. 18 and 18A, the details of trigger 98 are illustrated. Trigger 98 is preferably a single-piece, unitary component, which is injection molded from a polymeric material, such as nylon. Trigger 98 includes a gripping portion 146, a curved abutment portion 148 and a clearance aperture 150. The unitary body of trigger 98 defines a clearance hole 152 for receipt of pivot post 43b. Aperture 150 provides clearance for one (1) of the posts which receives a threaded fastener for joining together the two (2) housing halves (see FIG. 22). Abutment portion 148 cooperates with rear lever 41 (see FIG. 19) so as to prevent dispensing movement of the nine (9) plunger array 39 (i.e. forward depression), unless the tips of the needles are extended. Lever 41 includes a rib 154 and the positioning of rib 154 relative to abutment portion 148 prevents actuation of the lever 41 for medicant dispensing unless the abutment portion 148 is moved out of an abutment position, see FIGS. 2 and 3. Abutment portion 148 is sized, shaped and positioned such that essentially full deployment of the nine (9) needles 44 is required before portion 148 is moved out of an abutment position with rib 154 which would thereafter allow for the lever 41 to be used in the advancing movement of nine (9) plunger array 39.

Referring to FIGS. 19 and 19A, the details of lever 41 are illustrated. Lever 41 is preferably a single-piece, unitary component which is injection molded from a polymeric material, such as nylon. Lever 41 is actually illustrated as part of a lever assembly 155. The lever assembly 155 further includes a connection bar 156, which is attached to lever 41 using a threaded fastener at each end. Lever 41 includes gripping portion 158 and a pivot hub 160. Pivot hub 160 defines a through bore 162 which receives pivot post 43c. Connection bar 156 extends through the handle opening 164 of the nine (9) plunger array 39 (see FIG. 20). When movement of lever 41 is permitted by the orientation of trigger 98, the connection bar 156 moves forward in a distal direction. Lever 41 pivots forward about pivot post 43c as the gripping handle 166 of device 20 is squeezed. This squeezing action causes pivoting movement of lever 41 and thereby, advancing movement of plunger array 39. This movement causes each plunger 39a with its rubber sealing piston 168 attached, to move through its corresponding medicant chamber 36 of each barrel 35 for dispensing medicant through the nine (9) needles 44 and thereby injecting the medicant into the nine (9) tissue sites.

Figure 20:
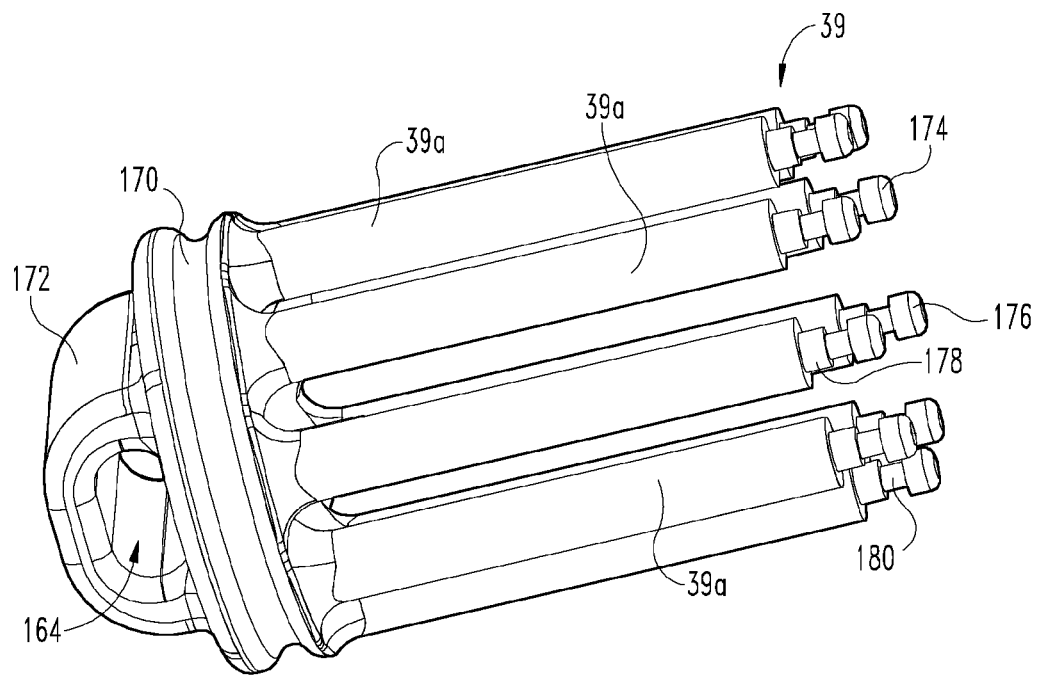
FIG. 20 is a perspective view of a plunger array which is one component part of the FIG. 1 injection device.
Figure 20A:
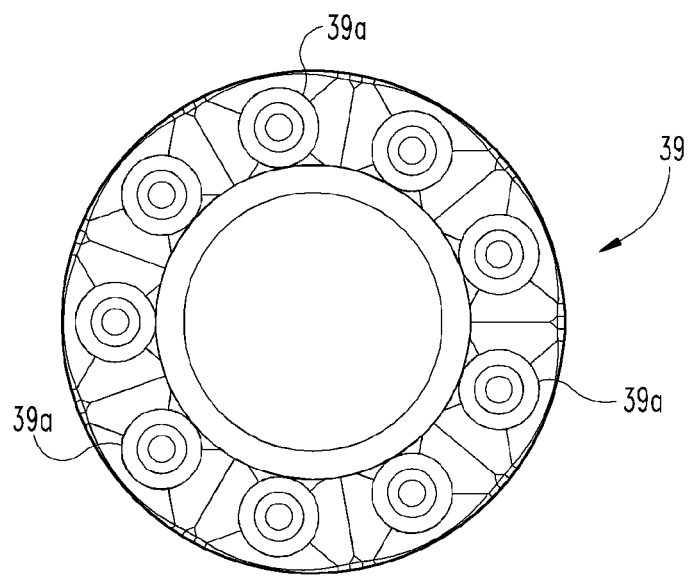
FIG. 20A is a distal end elevational view of the FIG. 20 plunger array.

Referring to FIGS. 20 and 20A, the details of the nine (9) plunger array 39 are illustrated. Plunger array 39 is preferably a single-piece, unitary component which is injection molded from a polymeric material, such as ABS, polyethylene or HDPE. Plunger array 39 includes a base 170 and a handle 172 joined to the base 170. Handle 172 defines handle opening 164. The nine (9) plungers 39a are each similarly sized and shaped and equally spaced in a cylindrical array as shown in FIG. 20A. The tip 174 of each plunger 39a has a hub-like shape with an enlarged head 176 and a similarly sized base 178. A reduced diameter post 180 is positioned therebetween. The combination of plunger array 39 and the nine (9) cooperating barrels 35 comprises the primary construction of the "syringe" of device 20.

Figure 21:
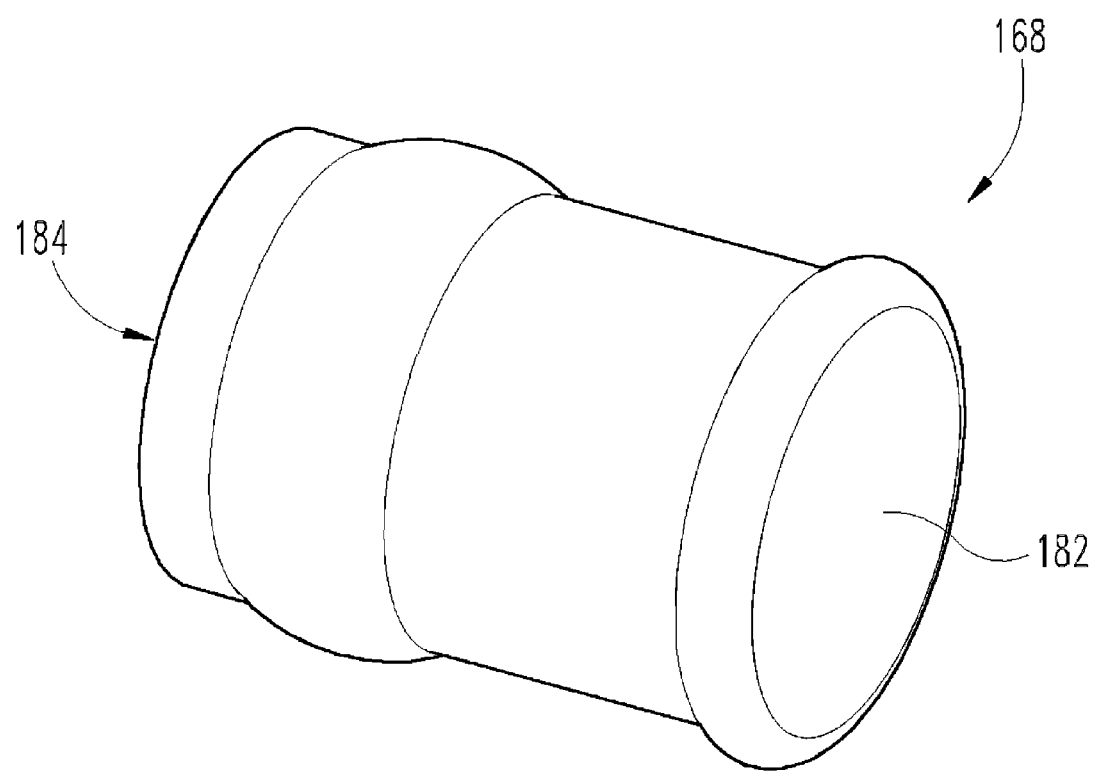
FIG. 21 is a perspective view of a piston which is one component part of the FIG. 1 injection device.

A hollow sealing piston 168 (see FIG. 21) is snapped onto each tip 174. Each sealing piston 168 (nine (9) total) is sized and shaped to securely fit onto its corresponding tip 174. A preferred material for the single-piece, unitary construction of sealing piston 168 is silicone rubber or polyisoprene. The size and shape of each head portion 182 are selected for a snug fit into the medicant chamber 36 of each barrel 35. End 184 is open for receiving tip 174. The size and shape selection for the referenced snug fit are important, as would be understood as part of conventional syringe technology. It is important as the individual plungers and pistons travel through each corresponding medicant chamber that the medicant present in that chamber be dispensed out through the tip and thereafter through the corresponding needle without any noticeable reverse leakage of the medicant past the edges of the head portion 182 of sealing piston 168.

Figure 23:
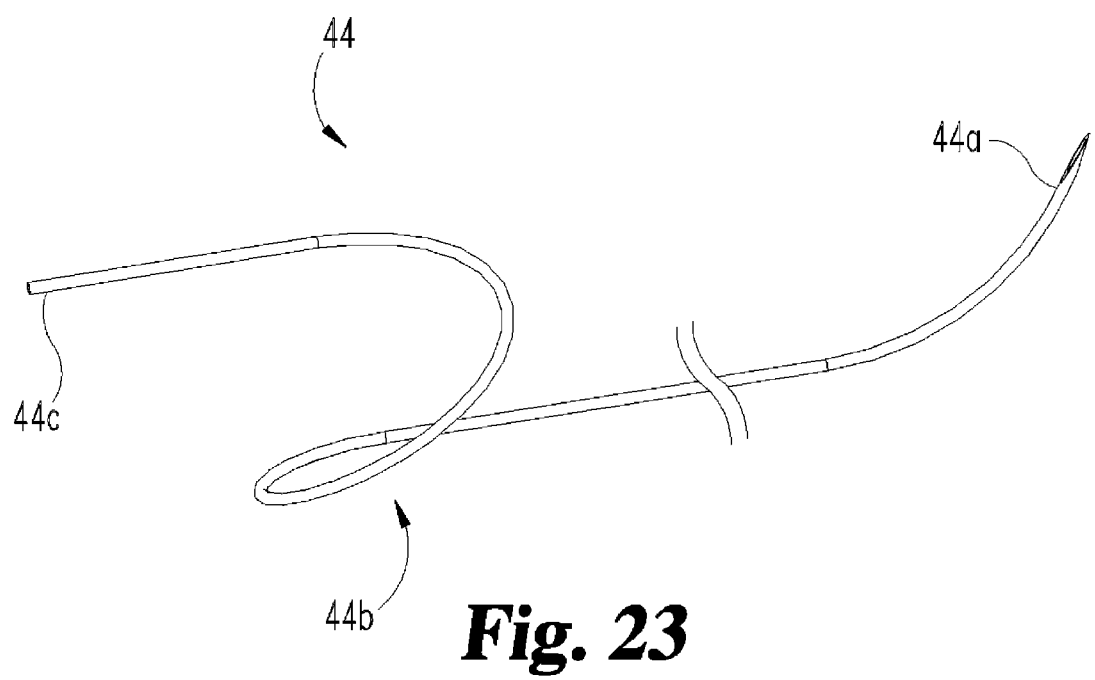
FIG. 23 is a perspective view of an injection needle which is one component part of the FIG. 1 injection device.

Referring to FIG. 23, the details of one of the nine needles 44 are illustrated. End 44c is the portion which is adhesively connected to the corresponding barrel 35. The loop 44b serves the function of providing additional length between end 44c and open tip 44a so that tip 44a is able to move independently of the fixed position of end 44c. The curved loop 44b may also provide a spring-biasing function to aid in the returning of trigger 98 to its starting position. Trigger 98 is squeezed toward lever 41 when it is intended to move yoke 96 and thereby advance the tips 44a of the needles. This movement tries to more tightly coil the loop 44b or tries to flex the loop 44b of each needle. The stiffness and memory of the needle metal causes each needle to try and restore the shape of the loop. This creates a type of spring return which pulls back on ring 88 and thus pulls back on yoke 96.

If the spring forces are sufficient to effect this movement, the trigger will return to its starting position once the gripping force of the user is removed. An additional spring may be located in the handle of device 20 if the needles alone are not sufficient for a "spring return" of the trigger.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. An injection device for injecting a medicant into a plurality of sites in a patient for a selected treatment, wherein the number of sites is the total number for the selected treatment thereby requiring a single positioning step, said injection device comprising:
   a body including a plurality of medicant barrels;
   a plurality of injection needles, wherein each needle of said plurality is connected to a corresponding one of said medicant barrels;
   a multi-lumen tip for positioning an open tip of each injection needle at a corresponding one of said injection sites;
   means for connecting said multi-lumen tip with said body; and
   means for moving each injection needle of said plurality of injection needles between a deployed, injection position and a retracted position, wherein the number of needles is at least as great as the number of sites for the selected treatment.

2. The injection device of claim 1 wherein said means for moving includes a control linkage with a multi-lumen ring which is connected to each injection needle.

3. The injection device of claim 1 which includes a plunger array having a plurality of plungers for receipt by said plurality of medicant barrels.

4. The injection device of claim 3 which further includes a corresponding barrel for each plunger of said plunger array.

5. The injection device of claim 4 which further includes a lever for moving said plunger array.

6. The injection device of claim 1 wherein each barrel defines a medicant chamber.

7. The injection device of claim 1 wherein each barrel defines a filling passage and a separate injection end.

8. The injection device of claim 1 wherein said means for connecting includes a multi-lumen shaft with a distal end connected to said multi-lumen tip.

9. The injection device of claim 1 wherein each needle includes a barrel-connection end, an open injection tip and a loop formed between said barrel-connection end and said open injection tip.

10. The injection device of claim 1 wherein the number of needles, the number of barrels, the number of plungers and the number of sites are all the same.

11. The injection device of claim 1 in combination with a filling syringe and a charge of medicant loaded into said filling syringe.

12. The injection device of claim 1 wherein said multi-lumen tip includes two portions which are joined together, each portion defining a plurality of grooves.

13. The injection device of claim 1 wherein each injection needle of said plurality of injection needles includes a barrel-connection and, and injection tip and a curled portion located between said barrel-connection end and said injection tip.

14. The injection device of claim 13 which further includes a deployment ring and wherein each injection needle of said plurality of injection needles is securely attached to said ring.

15. The injection device of claim 1 wherein said means for moving includes a cooperating arrangement of a ring, a trigger and a yoke.

16. The injection device of claim 1 wherein said means for moving includes a cooperating arrangement of component parts which are constructed and arranged to move said plurality of injection needles as a plurality.

17. The injection device of claim 1 which further includes means for injecting a medicant through each injection needle of said plurality of injection needles in a single step.

18. An injection device for injecting a medicant into a plurality of sites in a patient for a selected treatment, wherein the number of sites is the total number for the selected treatment thereby requiring a single positioning step, said injection device comprising:
   a body including a syringe and a control linkage, said syringe including a plurality of barrels and a cooperating plunger array including a plurality of plungers, wherein each barrel receives a corresponding plunger;
   a plurality of injection needles connected to said syringe wherein one injection needle is connected to each barrel;
   a multi-lumen tip;
   a shaft connected to said multi-lumen tip and extending between said multi-lumen tip and said body, said shaft receiving a portion of each injection needle; and
   said control linkage being connected to each needle and being constructed and arranged to move each needle relative to said multi-lumen tip between a deployed injection position and a retracted position, wherein the number of needles is at least as great as the number of sites for the selected treatment.

19. The injection device of claim 18 wherein the control linkage includes a multi-lumen ring and each needle is received by said multi-lumen ring and is connected to said multi-lumen ring.

20. The injection device of claim 18 which further includes a lever for moving said plunger array.

21. The injection device of claim 18 wherein each barrel defines a medicant chamber.

22. The injection device of claim 18 wherein each barrel defines a filling passage and a separate injection end.

23. The injection device of claim 18 wherein said shaft defines a needle-receiving channel for each injection needle.

24. The injection device of claim 18 wherein said multi-lumen tip defines a plurality of needle passages and a plurality of exit apertures.

25. The injection device of claim 18 wherein each needle includes a barrel-connection end, an open injection tip and a loop formed between said barrel-connection end and said open injection tip.

26. The injection device of claim 18 =wherein the number of needles, the number of barrels, the number of plungers and the number of sites are all the same number.

27. A method of preparing for use and using an injection device for injecting a medicant into a plurality of sites in a patient for a selected treatment, said method comprising the following steps:
providing a filling syringe;
providing a charge of medicant for delivery by said filling syringe;
providing an injection device having a plurality of barrels, a plunger array, a plurality of injection needles with one needle connected to each barrel, an injection tip which receives an open tip of each injection needle and means for moving each injection needle to a deployed injection position;
inserting said filling syringe into said injection device;
filling each barrel of said plurality of barrels with medicant;
moving said plunger array to purge air from within the plurality of injection needles;
retracting the open tip portion of each needle into said injection tip;
positioning said injection tip at the sites;
moving each injection needle to a deployed injection position into its corresponding site; and
moving said plunger array to inject medicant into each site.

28. The method of claim 27 wherein the number of needles, the number of barrels, the number of plungers and the number of sites are all the same number.

29. The method of claim 27 wherein the step of moving said plunger array to purge air is performed as a single step for said plurality of injection needles.

30. The method of claim 27 wherein the step of moving each injection needle to a deployed injection position is performed as a single step for said plurality of injection needles.

* * * * *